(12) United States Patent
Lim

(10) Patent No.: US 11,672,833 B2
(45) Date of Patent: Jun. 13, 2023

(54) EDIBLE BIRD'S NEST EXTRACT AND METHOD OF EXTRACTION

(71) Applicant: Kah Meng Lim, Singapore (SG)

(72) Inventor: Kah Meng Lim, Singapore (SG)

(*) Notice: Subject to any disclaimer, the term of this patent is extended or adjusted under 35 U.S.C. 154(b) by 0 days.

(21) Appl. No.: 17/145,046

(22) Filed: Jan. 8, 2021

(65) Prior Publication Data

US 2021/0137996 A1     May 13, 2021

Related U.S. Application Data

(62) Division of application No. 16/084,076, filed as application No. PCT/SG2017/050117 on Mar. 10, 2017, now Pat. No. 10,918,674.

(30) Foreign Application Priority Data

Mar. 11, 2016 (SG) .............. 10201601905R

(51) Int. Cl.
    *A61K 35/57*      (2015.01)
    *A61K 47/36*      (2006.01)

(52) U.S. Cl.
    CPC .............. *A61K 35/57* (2013.01); *A61K 47/36* (2013.01)

(58) Field of Classification Search
    None
    See application file for complete search history.

(56) References Cited

U.S. PATENT DOCUMENTS

| | | | |
|---|---|---|---|
| 4,071,408 A | 1/1978 | Flashner et al. | |
| 10,918,674 B2 * | 2/2021 | Lim ..................... | A61P 3/10 |
| 2021/0361720 A1 * | 11/2021 | Lim ..................... | A61K 35/57 |

FOREIGN PATENT DOCUMENTS

| | | |
|---|---|---|
| CN | 101284017 A | 10/2008 |
| CN | 101597598 A | 12/2009 |
| CN | 102362637 | 2/2012 |
| CN | 104498572 * | 4/2015 |
| CN | 104498572 A | 4/2015 |
| CN | 106235303 A | 12/2016 |

OTHER PUBLICATIONS

Careena, S. et al., "Preliminary Study on the Enzyme Digestion Method for Edible Bird Nest for Invitro Bioassay" Universiti Putra Malaysia (2016) 3 pages total.
Communication (International Preliminary Report on Patentability) issued in International Application No. PCT/SG2017/050117, dated Jan. 22, 2018, 13 pages total.
Communication (International Search Report and Written Opinion) issued in International Application No. PCT/SG2017/050117, dated May 25, 2017, 10 pages total.
Parikh, A. et al., "A Review on Applications of Maltodextrin in Pharmaceutical Industry" International Journal of Pharmacy and Biological Sciences (2014) vol. 4, Issue 4, pp. 67-74.
Roh, K.-B. et al., "Mechanisms of Edible Bird's Nest Extract-Induced Proliferation of Human Adipose-Derived Stem Cells" Evidence-Based Complementary and Alternative Medicine (2012) vol. 2012, 11 pages total.
Runckel, C.W., "A Bird in the Hand" Business in Asia (2017) https://web.archive.org/web/20160218140252/http:/Iwww.business-in-asia.com/industries/birdnest_for_health.html, 5 pages total.

* cited by examiner

*Primary Examiner* — Ralph J Gitomer
(74) *Attorney, Agent, or Firm* — Troutman Pepper Hamilton Sanders LLP

(57) ABSTRACT

The present invention relates to a method for preparing a bird's nest extract and the various extracts obtained from said method. In an aspect of the present invention, there is provided a method for preparing a bird's nest extract, the extract comprising at least one molecule obtained from edible bird's nest (EBN), the method comprising the steps of: (a) washing raw EBN; (b) filtering the washed EBN; (c) extracting the molecule from the EBN; and (d) isolating the molecule.

6 Claims, 26 Drawing Sheets

(24 of 26 Drawing Sheet(s) Filed in Color)

EDIBLE BIRD'S NEST EXTRACT AND METHOD OF EXTRACTION

CROSS-REFERENCE TO RELATED APPLICATIONS

This application is a divisional application of U.S. application Ser. No. 16/084,076, filed Sep. 11, 2018, which is a U.S. National Phase application under 35 U.S.C. § 371 of International Patent Application No. PCT/SG2017/050117, filed on Mar. 10, 2017, which claims priority to Singapore Patent Application No. SG 10201601905R, filed on Mar. 11, 2016, all of which applications are incorporated herein by reference in their entireties.

TECHNICAL FIELD OF INVENTION

The present invention relates to a method for preparing a bird's nest extract and the various extracts obtained from said method.

BACKGROUND OF INVENTION

Edible bird's nest (EBN) is the nest made from the saliva of swiftlets naturally found in the South-east Asian region. The abandoned nests are harvested from the wild or from specially built housing for swiftlets. It has been reported that EBN exhibited various bioactivities and nutritional value that include potential for mitogenic response, epidermal growth factor (EGF)-like activity, anti-influenza virus, haemagglutination-inhibitory activity, lectin-binding activity, improvement of bone strength and dermal thickness, and hormone content. Processing of EBN can be different depending on the application. Ongoing investigations have been carried out to elucidate the biological and medical functions of the edible bird's nest.

Currently, EBN is used in the form of a soup or other drinks by boiling the EBN in water and consuming. The molecules of EBN in such a scenario are large biomacromolecules that are difficult for the body to digest and absorb. As a result, the bioavailability of the beneficial components of EBN prepared in such a manner is low, and the beneficial effects of EBN is not maximised.

However, consuming whole EBN may lead to immunoglobulin E (IgE) mediated anaphylaxis (Goh et al., 2001, J. Allergy Clin. Immun., 107(6), 1082-1088) and EBN is thought to be the most common cause of food-induced anaphylaxis which could be life-threatening among children.

Another problem with crude EBN is the presence of undesirable compounds either due to natural causes or added intentionally during processing. Adulteration of EBN commonly takes place decreasing the quality of the EBN. Adulterants used include pig skin, agar, red seaweed and karaya gum. In order to camouflage adulterants and waste matters, bleaches are often added.

Of particular concern is the presence of nitrite salts which is derived mainly from the faeces of the swiftlets. Nitrites can also be added to white bird's nest during processing to turn it into red bird's nest which is commercially more valuable. Ingestion of excessive nitrites had been linked to cancer (Bryan et al. Food Chem. Toxicol. 2012, 50 (10), 3646-3654).

Viruses, bacteria and fungi could contaminate EBN in the wild or in the factory during processing. Concerns with regards to avian flu in wild birds can lead to restriction of imports of whole EBN itself.

Therefore, there is a need to improve the processing of EBN to improve the overall quality and beneficial properties to the consumer. By extracting and isolating desirable compounds from EBN, harmful effects are avoided or minimised while maximising the therapeutic benefits of EBN.

The listing or discussion of an apparently prior-published document in this specification should not necessarily be taken as an acknowledgement that the document is part of the state of the art or is common general knowledge.

Any document referred to herein is hereby incorporated by reference in its entirety.

SUMMARY OF INVENTION

In a first aspect of the present invention, there is provided a method for preparing a bird's nest extract, the extract comprising at least one molecule obtained from edible bird's nest (EBN), the method comprising the steps of: (a) washing raw EBN; (b) filtering the washed EBN; (c) extracting the molecule from the EBN; and (d) isolating the molecule.

Preferably, the washing step comprises exposing the EBN to a first enzyme solution at ambient temperatures for about 5 minutes and soaking the EBN and enzyme solution in water for a further 5 minutes. More preferably, the first enzyme solution comprises a nitrite reductase. In an embodiment, the water may be obtained from a reverse osmosis process. The washing step may involve washing the EBN in oxygenated water for about 10 minutes followed by a drying period for about 12 hours at 70° C.

Preferably, the method further comprising sterilising the washed EBN prior to the extraction step at 121° C. for about 10 minutes. Alternatively, the extraction process may be carried out for about 20 minutes.

The extraction solution may comprising any one selected from the group comprising: an anti-N glycan, an anti-O glycan, an anti-sialic acid (particularly a sialic acid binding Ig-like Lectin 14), an anti-zinc finger, an anti-perlecan, an anti-helix-turn-helix, an anti-hyaluronan, an anti-decorin, an anti-dermatan, an anti-chondroitin, an anti-lumican, an anti-keratan, an anti-syndecan, an anti-leucine zipper, an anti-heparan sulphate, an anti-brevican, an anti-neurocan, an anti-versican.

By "anti-", it is meant to refer to any molecule that selectively targets and binds to the target of interest, i.e. the target being a glycan (N or O glycan), a sialic acid (particularly an anti-sialic acid binding Ig-like Lectin 14), an anti-zinc finger, an anti-perlecan, an anti-helix turn helix, an anti-hyaluronans, an anti-decorin, an anti-dermatan, an anti-chondroitin, an anti-lumican, an anti-keratan, an anti-syndecan, an anti-leucine zippers, an anti-heparan sulphate, an anti-brevican, an anti-neurocan, an anti-versican etc.

As such, it follows that the extraction solution of the present invention will give rise to an EBN extract comprising any one selected from the group: an N glycan, an O glycan, an sialic acid (particularly a sialic acid binding Ig-like Lectin 14), a zinc finger, a perlecan, a helix-turn-helix, a hyaluronan, a decorin, a dermatan, a chondroitin, a lumican, a keratan, a syndecan, a leucine zipper, a heparan sulphate, a brevican, a neurocan, a versican. These may be present in the extract in any suitable amounts. In various embodiments, the composition may include any one of the following:

(a) EBN Extract 1
20% N glycans
30% O glycans
50% sialic acid binding Ig-like Lectin 14

(b) EBN Extract 2
70% zinc fingers
15% perlecans
15% N glycans
(c) EBN Extract 3
15% N glycans
25% helix turn helix
15% hyaluronans
35% decorin
10% dermatan
(d) EBN Extract 4
10% dermatan
15% chondroitin
55% hyaluronans
20% lumican
(e) EBN Extract 5
10% keratan
25% syndecans
35% chondroitin
30% hyaluronans
(f) EBN Extract 6
35% leucine zippers
30% decorin
35% lumican
(g) EBN Extract 7
25% heparan sulphate
15% brevican
20% neurocan
20% versican
20% decorin.

These amount percentages may be weight percentage of the entire composition or otherwise.

Preferably, in an embodiment, extracting the molecule is carried by exposing the washed EBN to any one of an extraction solution selected from the group comprising:
(a) a solution comprising an anti-N glycan and an anti-O glycan;
(b) a solution comprising an anti-heparan sulphate, an anti-chondroitin, an anti-keratan, and an anti-dermatan; and
(c) a solution comprising an anti-leuzine zipper, an anti-helix-turn-helix, and an anti-zinc finger.

The amount present in each solution (a) to (c) above may be:
(a) 50% anti-N glycan and 50% anti-O glycan;
(b) 25% anti-heparan sulphate, 25% anti-chondroitin, 25% anti-keratan, and 25% anti-dermatan; and
(c) 37% anti-leucine zipper, 33% anti-helix-turn-helix, and 30% anti-zinc finger.

In addition, in alternative embodiments, the compositions of the extraction solution may be any one selected from the following:
(a) Composition 1
20% anti-N glycans (molecular weight between 20 kDa to 1000 kDa)
30% anti-O glycans (molecular weight between 30 kDa to 3000 kDa)
50% anti-sialic acid binding Ig-like Lectin 14 (molecular weight between 20 kDa to 700 kDa); or
(b) Composition 2
70% anti-zinc fingers (molecular weight between 10 kDa to 200 kDa)
15% anti-perlecans (molecular weight between 50 kDa to 10000 kDa)
15% anti-N glycans (molecular weight between 20 kDa to 700 kDa); or
(c) Composition 3
15% anti-N glycans (molecular weight between 20 kDa to 700 kDa)
25% anti-helix turn helix (molecular weight between 10 kDa to 300 kDa)
15% anti-hyaluronans (molecular weight between 100 kDa to 3000 kDa)
35% anti-decorin (molecular weight between 10 kDa to 200 kDa)
10% anti-dermatan (molecular weight between 50 kDa to 500 kDa); or
(d) Composition 4
10% anti-dermatan (molecular weight between 50 kDa to 500 kDa)
15% anti-chondroitin (molecular weight between 30 kDa to 700 kDa)
55% anti-hyaluronans (molecular weight between 100 kDa to 3000 kDa)
20% anti-lumican (molecular weight between 20 kDa to 250 kDa); or
(e) Composition 5
10% anti-keratan (molecular weight between 25 kDa to 500 kDa)
25% anti-syndecans (molecular weight between 20 kDa to 100 kDa)
35% anti-chondroitin (molecular weight between 30 kDa to 700 kDa)
30% anti-hyaluronans (molecular weight between 100 kDa to 3000 kDa); or
(f) Composition 6
35% anti-leucine zippers (molecular weight between 10 kDa to 300 kDa)
30% anti-decorin (molecular weight between 10 kDa to 200 kDa)
35% anti-lumican (molecular weight between 20 kDa to 250 kDa); or
(g) Composition 7
25% anti-heparan sulphate (molecular weight between 30 kDa to 300 kDa)
15% anti-brevican (molecular weight between 10 kDa to 300 kDa)
20% anti-neurocan (molecular weight between 20 kDa to 300 kDa)
20% anti-versican (molecular weight between 50 kDa to 500 kDa)
20% anti-decorin (molecular weight between 10 kDa to 200 kDa).

Each composition may be different specificities, effects and hence, uses. A summary for each composition is as follows:

Composition 1

This unique composition provides an EBN's extract that at the minimal concentrations of 0.5 g/l and 1 g/l could inhibit haemagglutination for H1N1 and H3N2 respectively. Similar extract with only sialic acid could inhibit haemagglutination for H1N1 and H3N2 respectively ONLY at minimal concentrations of 5 g/l to 160 g/l.

Secondly, for the in vitro infectivity of influenza H1N1, it is shown that the addition of this composition at concentrations between 0.03 to 2 g/l to mammalian cells reduced the virus titer generated by at least 2 fold when compared to the culture without the extract composition supplementation. Similar extract with only sialic acid could only do so at concentrations 10 to 464 g/l, at much higher concentrations.

This shows that this extraction solution can extract a composition (i.e. the EBN extract) that is potent for the prevention of influenza viruses, much more potent than any sialic acid or compound in the market.

It is also shown that mammalian cells after 1 day infection with H1N1 and H3N2 influenza viruses in the presence of minimal concentration of 0.33 g/l, no cytopathic effects were observed.

Other competitors, i.e. other commercial EBN solutions were also tested in the haemagglutination inhibition assay with influenza A. These EBN solutions were found to be either cytotoxic to the cells or did not exhibit any detectable anti influenza virus activity. In conclusion, GeneOasis' proprietary EBN extract is potent and superior in the prevention of influenza virus infection.

Composition 2

This unique composition provides an EBN extract that provides enhanced kidney cell growth in a concentration dependent manner when compared to the control without this GO's proprietary EBN extract composition. In the presence of 3.3 g/l of this composition, kidney cells reached the confluent cell density on day 3 ($\sim$5×10$^5$ cells/cm2) earlier than the control (Day 4). The growth enhancement can be related to the presence of active molecules found in this unique EBN extract.

Composition 3

This extraction composition provides an EBN extract that can elicit an increase in human stem cell proliferation during cell expansion in vitro.

Most importantly, comparing the present extract to Competitor A EBN by protein amount revealed that 4.39% GeneOasis EBN can induce a cell growth curve that is statistically significantly different from 10% Competitor A EBN, starting from day 2 through day 5 of culture (*** p<0.001 for all days; p values are shown on the graph). Similarly, comparing GeneOasis EBN (GOA) to Competitor A EBN by volume revealed that 10% the present EBN extract can induce a cell growth curve that is statistically significantly different from 10% Competitor A EBN, starting from day 2 through day 5 of culture (p values are shown on the graph). This is significant and novel as it shows that the present EBN extracts are more potent than Competitor A EBN in (i) promoting cell growth and not causing cell death like that of Competitor A, and (ii) its ability to replace EGF.

Most importantly, comparing the present EBN extract (GOB) to Competitor B EBN by protein amount revealed that 3.35% of the present EBN extract can induce a cell growth curve that is statistically significantly different from 10% Competitor B EBN, starting from day 4 through day 5 of culture ( p<0.01 for day 4 and * p<0.001 for day 5; p values are shown on the graph). Similarly, comparing the present EBN extract (GOB) to Competitor B EBN by volume revealed that 10% of the present EBN extract can induce a cell growth curve that is statistically significantly different from 10% Competitor A EBN, starting from day 2 through day 5 of culture ( p<0.01 for day 4 and * p<0.001 for day 2 and day 5; p values are shown on the graph). This is significant and novel as it shows that the present EBN extracts are more potent than Competitor B EBN in (i) promoting cell growth, and (ii) its ability to replace EGF, particularly at later stages of cell growth (day 4 and day 5 of culture).

Composition 4

This composition provides an EBN extract that can elicit a statistically significant increase in human stem cell proliferation during the course of chondrogenic differentiation in vitro. This is novel as this is the first study to show not only an increase but also a statistically significant increase in DNA (cellular proliferation).

Composition 5

This composition provides an EBN extract that elicits an increase in human stem cell chondrogenic differentiation in terms of proteoglycan content in vitro.

Addition of the present EBN extracts lead to an increase in glycosaminoglycan (GAG) content per pellet and GAG/DNA ratio, mostly from day 14 to day 28 of differentiation. The increase in GAG content per pellet is most significant and most consistent from day 14 to day 28 of differentiation using 2.5% to 5%. The increase in GAG/DNA ratio is most significant and most consistent from day 14 to day 28 of differentiation using 5% of EBN. GAG is a major type of proteoglycan commonly found in cartilage tissue.

Composition 6

This composition provides an EBN extract that leads to an increase in Collagen II content per pellet and Collagen II/DNA ratio, mostly from day 21 to day 28 of differentiation. The increase in Collagen II content per pellet is most significant and most consistent for 1.25% EBN from day 7 to day 14, as well as for 2.5% EBN from day 21 to day 28 of differentiation. The increase in Collagen II/DNA ratio is most significant and most consistent from day 7 to day 28 of differentiation using 1.25% EBN. Collagen II is a major type of collagen molecule or fibrils commonly found in articular cartilage tissue. Collagen II content per pellet is indicative of the total functional output of stem cell-derived chondrocyte-like cells in vitro. Collagen II/DNA ratios reflect Collagen II production per cell and are used as functional indicators of how well the stem cells are differentiating into chondrocyte-like cells. Dotted lines refer to Collagen II per pellet and Collagen II/DNA ratios when no EBN extracts were added.

Composition 7

This extraction solution composition provides an EBN extract that contain EGF-like component, which can be beneficial to long term culturing of hNPC.

Preferably, the step of extraction is carried out in the presence of an acid.

Preferably, the extraction is carried out at between 25° C. to 37° C. for about 20 to 120 minutes.

Preferably, isolating the molecule is carried out in the presence of a second enzyme solution. More preferably, second enzyme solution comprises a vegetable or fruit protease. The concentration of the second enzyme solution may be between 10 ug/ml to 100 ng/ml. Further, the step of isolating the molecule is carried out at 45° C. for 60 minutes at pH 6.5 to 9.0.

Preferably, the isolation step further comprising heating the mixture at 70° C. for 5 minutes to deactivate the enzymes in the second enzyme solution.

Preferably, the present method further comprising the step of dehydrating the extracted mixture. More preferably, the dehydrating step is freeze drying.

In a second aspect of the present invention, there is provided a bird's nest extract obtained from a method according to the first aspect of the present invention.

In a third aspect of the present invention, there is provided a composition comprising an extract according to the second aspect of the present invention. Preferably, the composition further comprises a maltodextrin. In an embodiment, the amount of maltodextrin present in the composition may be between 30 wt % to 75 wt %.

In an embodiment of the present invention, the extract may be used in medicine. More particularly, the extract may be used in the manufacture of a medicament for the treatment and/or prevention of a condition and/or disease.

Even more particularly, the extract may be used to improve the skin and treat various skin ailments, dehydration and inflammatory skins, boost the immune system, delay aging, promote metabolism, protect a person's visual sight, improve blood circulation, regulate blood cholesterol level, protect cardiovascular health, invigorate and renew cells, ease arthritis discomfort, balance hormone levels, reduce incidence of Inflammation, control diabetes, treat degenerative joints, degenerative skin, degenerative nervous system and the brain, and protect from kidney failure.

In a fourth aspect of the present invention, there is provided a pharmaceutical composition comprising an extract according to the second aspect of the invention a pharmaceutically-acceptable carrier, excipient or diluent.

Preferably, the composition or formulation is a unit dosage containing a daily dose or unit, daily sub-dose or an appropriate fraction thereof, of the active ingredient. The compositions of the present invention may normally be administered orally or by any parenteral route, in the form of a pharmaceutical composition comprising the bird's nest extract, optionally in the form of a non-toxic organic, or inorganic, acid, or base, addition salt, in a pharmaceutically acceptable dosage form. Depending upon the condition, disorder and patient to be treated, as well as the route of administration, the compositions may be administered at varying doses.

In human therapy, the bird's nest extract or compositions of the invention can be administered alone but will generally be administered in admixture with a suitable pharmaceutical excipient diluent or carrier selected with regard to the intended route of administration and standard pharmaceutical practice. They may be administered orally (via tablets and capsules) or parenterally, for example, intravenously, intra-arterially, intraperitoneal, intrathecal, intraventricular, intrastemally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Compositions or formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Alternatively, the compositions of the invention can be administered in the form of a suppository or pessary, or they may be applied topically in the form of a lotion, solution, cream, ointment or dusting powder. The compositions of the invention, particularly the bird's nest extracts, may also be transdermal administered, for example, by the use of a skin patch. They may also be administered by the ocular route, particularly for treating diseases of the eye. For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyl-dodecanol, benzyl alcohol and water.

Generally, in humans, oral or topical administration of the compositions of the invention is the preferred route, being the most convenient. In circumstances where the recipient suffers from a swallowing disorder or from impairment of drug absorption after oral administration, the drug may be administered parenterally, e.g. sublingually, buccally, transmucosal or transdermal means.

Currently, bioactive molecules like Chondroitin Sulfate (CS), Keratan Sulfate (KS) and Hyaluronic Acid (HA) which are widely used in supplementing joint cartilage health are extracted mainly from animal parts or genetically modified microorganisms cloned in bioreactors. There is a lack of a standard for consistency in purity and yields and safety aspects of the extracted products.

When these compounds are extracted from natural sources of edible bird nests (EBN) it resolves the issue of safety and sustainability, as EBN are very rich and abundant sources for such bioactive factors.

Chondroitin sulphate is used in arthritis treatment in the form of cream, capsules and health supplement medications. Hyaluronic Acid is used widely in cosmetic and pharmaceutical industries globally.

Absorption through the skin and joint, capsules or through the oral route of administration for such water soluble factors (CS), (KS) and (HA) has been a problem due to the poor permeability through hydrophobic membranes or structures in the skin or intestine. Thus it is difficult for the maximum and immediate effects of these compounds to reach the requisite sites in the body for millions of global sufferers of joint inflammation and pain. This has been a huge challenge for a sustainable and long term solution.

Through the process of separating compounds and their hydrolysis products such as chondroitin sulfate, hyaluronic acid, and keratan sulfate, an economical method is provided to supply the compounds in high purity and variable dosage to suit the purpose. The products isolated in this process is amenable to be delivered to the user in a variety of ways and methods to allow for effective and quick delivery of the compounds to the site of action. Especially with a suitable formulation, chondroitin sulfate, hyaluronic acid, and keratan sulfate can be delivered in effective and useful doses to the sites of pain and inflammation.

Formulated in lipid forms, the present extract may be used to produce a first economical product in the market that is transdermal and is composed of safe and sustainable bioactive molecules, extracted from natural but abundant supplies of EBN recycled crumbs.

In order that the present invention may be fully understood and readily put into practical effect, there shall now be described by way of non-limitative examples only preferred embodiments of the present invention, the description being with reference to the accompanying illustrative figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF INVENTION

Figure 1:
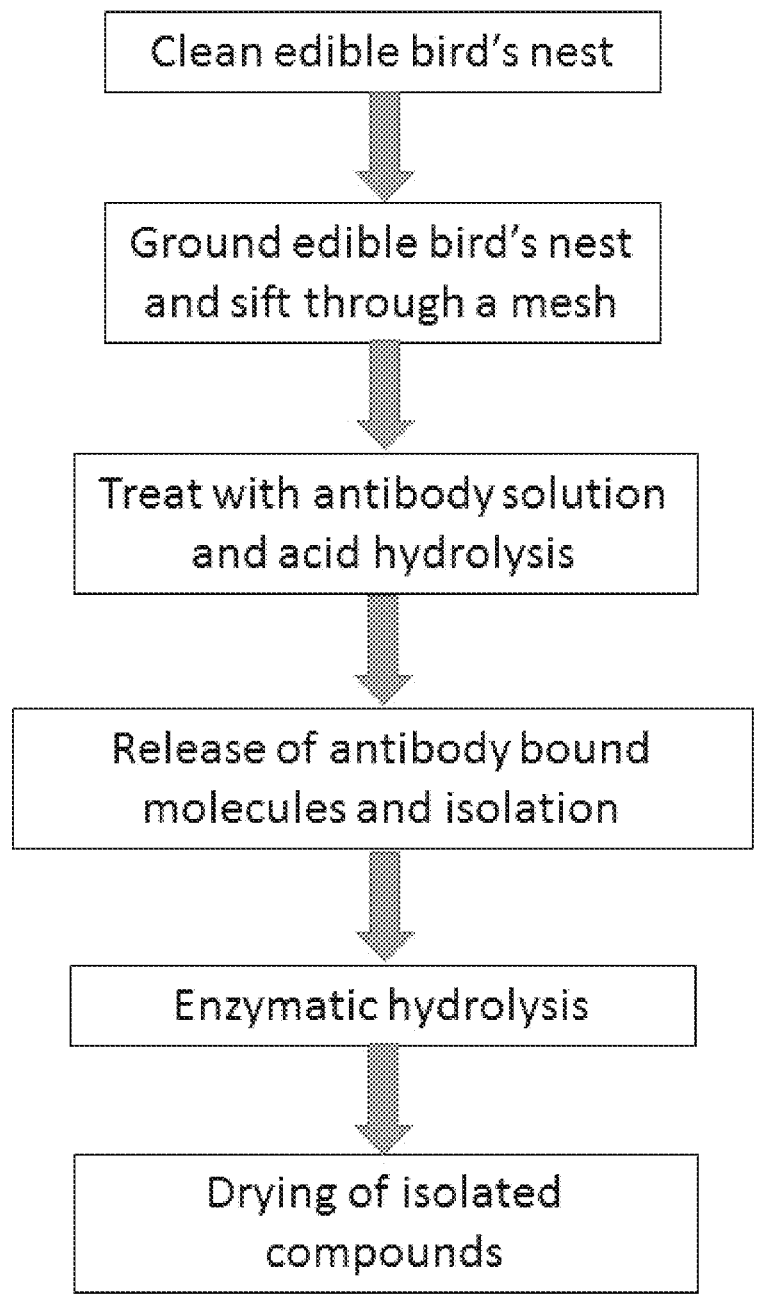
FIG. 1 shows a flow chart of a method of preparing a bird's nest extract according to an embodiment of the present invention.

In the present invention, a way to utilise EBN as a low cost source of active nutraceutical ingredients (ANIs) and yet having high efficacies such as active pharmaceutical ingredients (APIs) is presented.

Ambient or room temperature refers to a temperature in the range of 20 to 30° C.

N-linked glycans refer to structures wherein the nitrogen in the side chain of asparagine in the sequence Asn-X-Ser or Asn-X-Thr, where X is any amino except proline, forms a glycosidic bond with a glycan and the glycan may be composed of N-acetyl galactosamaine, galactose, neuraminic acid, N-acetylglucosamine, fucose, mannose, and other monosaccharides (Varki A, Cummings R D, Esko J D, et al., editors, Essentials of Glycobiology, 2nd edition, Cold Spring Harbor (NY): Cold Spring Harbor Laboratory Press; 2009).

O-linked glycans refer to structures wherein the oxygen in the side chain of serine or threonine forms a glycosidic bond with N-acetyl-galactosamine which is attached to additional sugar monosaccharides.

Heparan sulfate (HS) is a glycosaminoglycan defined by the disaccharide unit (GlcNAcα1-4GlcAβ1-4/IdoAα1-4)$_n$, containing N- and O-sulfate esters at various positions, and typically found covalently linked to a proteoglycan core protein. The main disaccharide units that occur in heparan sulfate are shown structurally below.

Disaccharide Units Found in Heparan Sulfate

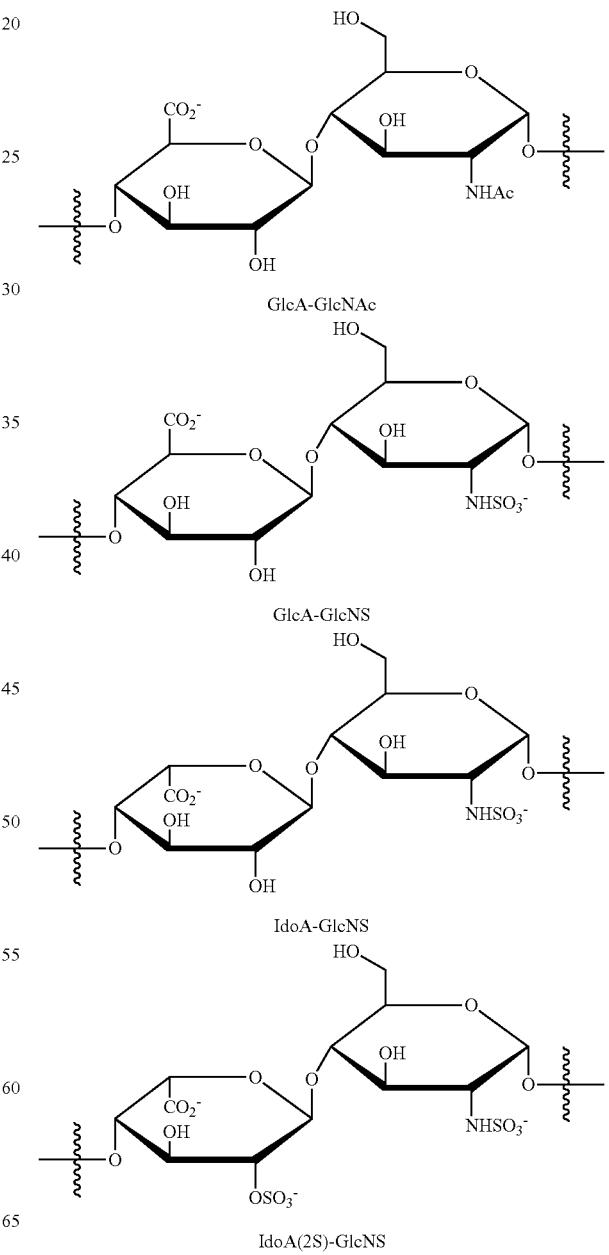

GlcA-GlcNAc

GlcA-GlcNS

IdoA-GlcNS

IdoA(2S)-GlcNS

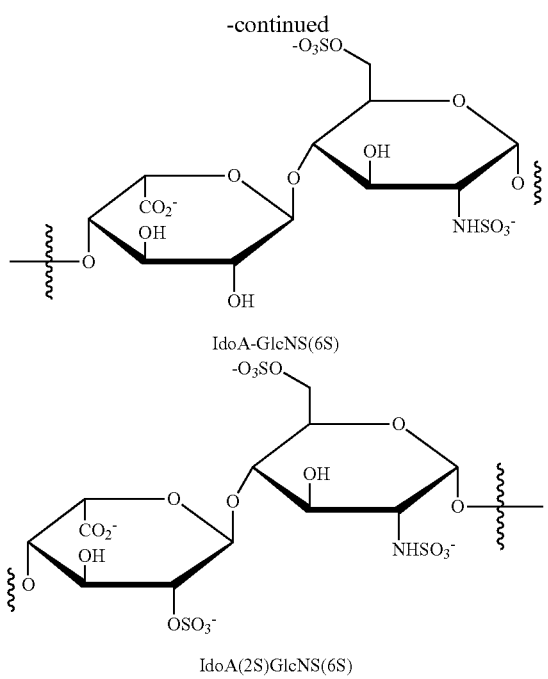

IdoA-GlcNS(6S)

IdoA(2S)GlcNS(6S)

Abbreviations

GlcA=β-D-glucuronic acid
IdoA=α-L-iduronic acid
IdoA(2S)=2-O-sulfo-α-iduronic acid
GlcNAc=2-deoxy-2-acetamido-α-D-glucopyranosyl
GlcNS=2-deoxy-2-sulfamido-α-D-glucopyranosyl
GlcNS(6S) 2-deoxy-2-sulfamido-α-D-glucopyranosyl-6-O-sulfate The most common disaccharide unit within heparan sulfate is composed of D-glucuronic acid (GlcA) linked to N-acetylglucosamine (GlcNAc) typically making up around 50% of the total disaccharide units. Not shown are the rare disaccharides containing a 3-O-sulfated glucosamine (GlcNS(3S,6S) or a free amine group (GlcNH$_3^+$).

Chondroitin sulfate is a sulfated glycosaminoglycan (GAG) defined by the disaccharide unit (GalNAcβ1-4GlcAβ1-3)$_n$ with a general structural formula I, modified with ester-linked sulfate at certain positions and typically found covalently linked to a proteoglycan core protein. A chondroitin chain can have over 100 individual sugars, each of which can be sulfated in variable positions and quantities.

Formula (I)

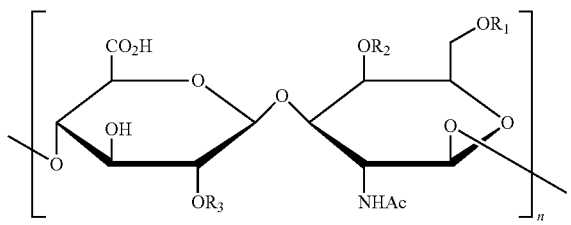

R$_1$, R$_2$, R$_3$ can be either H or SO$_3$H

Dermatan sulfate is a sulphated glycosaminoglycan like chondroitin sulfate wherein D-glucuronic acid is replaced by L-iduronic acid and the disaccharide monomer is shown in general structural formula II.

Formula (II)

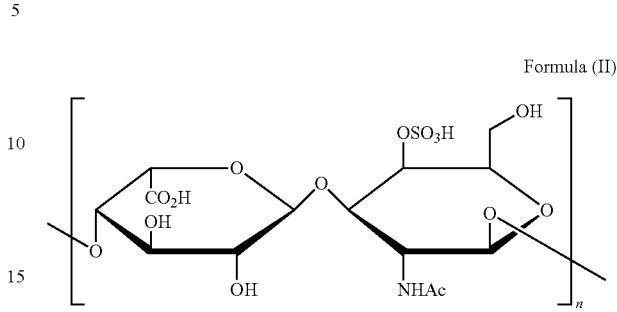

Keratan sulfate (KS) is a linear polysaccharide that consists of a repeating disaccharide unit. Keratan sulfate occurs as a proteoglycan (PG) in which KS chains are attached to cell-surface or extracellular matrix proteins. The basic repeating disaccharide unit within keratan sulfate is (-3Galactoseβ1-4-N-acetylglucosamineβ1-). This can be sulfated at carbon position 6 (C6) of either or both the Gal or GlcNAc monosaccharides. However, the detailed primary structure of specific KS types are best considered to be composed of three regions: a linkage region, at one end of which the KS chain is linked to the protein, a repeat region, composed of the -3Galβ1-4GlcNAcβ1- repeating disaccharide unit and a chain capping region, occurring at the opposite end of the KS chain to the protein linkage region.

Hyaluronic acid is an anionic, non-sulfated glycosaminoglycan distributed widely throughout connective, epithelial, and neural tissues. It is unique among glycosaminoglycans in that it is non-sulfated, and can be very large with its molecular weight often ranging in size from 5 to 20 kDa in vivo. Hyaluronic acid is a polymer of disaccharides, composed of D-glucuronic acid and D-N-acetylglucosamine, linked via alternating β-1,4 and β-1,3 glycosidic bonds.

Heparan sulfate, chondroitin sulfate, dermatan sulfate, keratan sulfate, hyaluronic acid are types of N or O-glycans as the sugar parts join to a protein at Asn or Ser/Thr.

Leucine zippers are a dimerization domain of the bZIP (Basic-region leucine zipper) class of eukaryotic transcription factors. The bZIP domains is 60 to 80 amino acids in length with a highly conserved DNA binding basic region and a more diversified leucine zipper dimerization region. The leucine zipper is a common three-dimensional structural motif in proteins and has that name because every seven amino acids is a leucine in the dimerization domain.

In proteins, the helix-turn-helix (HTH) is a major structural motif capable of binding DNA. It is composed of two α-helices joined by a short strand of amino acids and is found in many proteins that regulate gene expression.

A zinc finger is a small protein structural motif that is characterized by the coordination of one or more zinc ions in order to stabilize the fold. In general, zinc fingers coordinate zinc ions with a combination of cysteine and histidine residues. Originally, the number and order of these residues was used to classify different types of zinc fingers (e.g., Cys$_2$His$_2$, Cys$_4$, and Cys$_6$). More recently, a more systematic method has been used to classify zinc finger proteins instead. This method classifies zinc finger proteins into "fold groups" based on the overall shape of the protein backbone in the folded domain. The most common "fold groups" of zinc fingers are the Cys$_2$His$_2$-like (the "classic zinc finger"), treble clef, and zinc ribbon (Krishna S S, Majumdar I, Grishin N V, 2003, Nucleic Acids Research 31 (2), 532-50).

For naturally occurring glycan-binding proteins (GBP), excluding glycan specific antibodies, it is possible to classify GBPs broadly into two major groups—lectins and glycosaminoglycan binding proteins. Most lectins are members of families with defined "carbohydrate-recognition domains" (CRDs) that apparently evolved from shared ancestral genes, often retaining specific features of primary amino acid sequence or three-dimensional structure. Thus, new family members can be identified by searching protein sequence or structural databases. Despite this ability to predict new GBPs, the structures of glycans recognized by members of a single lectin family can be quite diverse. Single-site-binding affinities in many lectins appear to be low (with $K_d$ values in the micromolar range), although some lectins recognize glycans with much higher affinity (with $K_d$ values in the nanomolar range). For those lectins with low affinity, multivalent interactions between multiple CRDs and multiple glycans are often required to produce the high-avidity binding interactions that are relevant in vivo. Lectins tend to recognize specific terminal aspects of glycan chains by fitting them into shallow, but relatively well-defined, binding pockets. In contrast, protein interactions with sulfated glycosaminoglycans seem to involve surface clusters of positively charged amino acids that line up against internal regions of extended anionic glycosaminoglycan chains. The lectins can be further categorised as R-type, L-type, P-type, C-type, I-type, and galectins. Examples of N-glycans recognised by some lectins are shown structurally. The determinants required for binding are indicated in the boxed areas.

The general process to extract and isolate the ANIs from EBN is as follows (shown in FIG. 1):
  (a) Clean EBN to remove contaminants.
  (b) The cleaned EBN was grounded and sifted through a mesh.
  (c) The EBN powder was dissolved in water and treated with a solution containing at least one antibody.
  (d) The antibody and bound molecules may be separated
  (e) The bounded molecules were hydrolysed partially with an acidic solution, and the bounded molecules were released by addition of peptides of large molecular weight.
  (f) The released small molecules were isolated via dialysis.
  (g) The isolated fraction was treated with an enzymatic solution to further break down the compounds.
  (h) After denaturation and removal of the enzymes, the isolated fraction was dried to obtain a solid product.

The crude EBN (1 piece is approximately 10 to 50 g) is cleaned by soaking in water to remove nitrites, mites and other contaminants. The other possible contaminants that are removed may include heavy metals, bleach and other minute debris, including stains.

An effective method to remove the nitrites is to use a solution containing nitrite reductase enzymes from fruits, plants and soil. Additionally, the solution may contain another enzyme to inactivate any accompanying bacteria that produce the nitrite. To remove mites, a solution containing special fruit proteases are used. Such examples include any such protease from papaya (papain), kiwifruit (actinidin), pineapple (bromelain), fig (ficin) etc. These proteases may be used in any suitable concentration that will allow for the inactivation of the bacteria.

The EBN mixture was treated sequentially with each enzymatic solution for at least 5 minutes from room temperature to 40° C. Nanobubbling of the resultant suspension of EBN in the enzymatic solution will cause the degraded cellular debris to float to the surface of the water where it can be easily removed. The enzymatic solution is subsequently removed from the solid EBN. The solid EBN can be further washed to remove any residual enzymes and contaminants.

The cleaned EBN is dried to remove excess water, preferably at 70° C. for 12 h.

The cleaned EBN is grounded and sifted through a mesh. The size of the mesh should be sufficient to remove any large impurities left, preferably in a size of 200 to 700 μm. Most preferably the mesh size is 600 μm.

The EBN powder is placed in water, preferably distilled or deionised water, at 5° C. for 5 hours. A suitable concentration is 25 g of EBN in 1000 mL of water. The mixture may be further sterilised at 121° C. for 10 minutes if desired.

The EBN mixture is treated with an aqueous solution containing at least one antibody in a temperature range from 4 to 37° C. for at least 20 minutes. With a temperature of 25 to 37° C., 20 to 120 minutes suffice. With a temperature of 4° C., the mixture of antibody and EBN is kept for at least 9 hours. Generally, the lower the temperature the longer the time required for the antibody solution to completely bind to the targeted compounds.

The antibody/antibodies is selected from the following:
  1. Anti-N-glycans
  2. Anti-O-glycans
  3. Anti-Heparan sulfate (sulphate)
  4. Anti-Chondroitin sulfate (sulphate)
  5. Anti-Keratan sulfate (sulphate)
  6. Anti-Dermatan sulfate (sulphate)
  7. Anti-Leucine zippers
  8. Anti-Helix-Turn-Helix
  9. Anti-Zinc fingers
  10. A hyaluronic acid antibody The antibody and bounded molecules can be separated from the mixture by any of the commonly known methods. Some of these methods include physicochemical fractionation, class-specific affinity and antigen-specific affinity. Physicochemical fractionation includes differential precipitation, size-exclusion or solid-phase binding of immunoglobulins based on size, charge or other shared chemical characteristics of antibodies. Class-specific affinity includes solid-phase binding of particular antibody classes (e.g. IgG) by immobilised biological ligands that have specific affinity to immunoglobulins. Antigen-specific affinity includes using specific antigens to purify antibodies through their specific antigen-binding domains.

The antibodies to be used may include naturally occurring antibodies, or modified antibodies for example tagged antibodies that can facilitate the separation of the antibodies. Some common examples of tags used with antibodies are His-tag and FLAG-tag. Additionally, the antibody used to extract the target molecule could be bound to a solid support. The solid support could be made of a ferromagnetic material or conventional inert support material. The antibodies are commercially available and can be used as such. If modifications of the antibodies are desired, there are many methods as commonly known in the literature to modify the antibodies to obtain the desired characteristics. Antibody separation is commonly employed to extract out target proteins in a "fishing" method.

After addition of antibodies for a period of time as described previously, the mixture is treated with an acidic solution and heated to 100° C. to cause partial hydrolysis of the target compounds. The acid is preferably a food acid, for example citric acid, malic acid, acetic acid, tartaric acid, fumaric acid, and lactic acid. The mixture is cooled to room temperature and neutralised to a pH of 7.

The antibody bounded compounds are released from the antibody by adding excess larger peptides of natural glycoaminoglycans and cellular transcriptional regulators.

The released compounds are subsequently isolated from the added peptides, enzymes and antibodies via the use of a dialysis bag.

In another embodiment, the antibody solution may contain at least two antibodies. For instance, a solution containing Anti-N-glycans and Anti-O-glycans, a solution containing Anti-heparan sulfate, Anti-chondroitin, Anti-keratan, and Anti-dermatan, a solution containing Anti-leucine zippers, Anti-Turn-Helix-Turn, and Anti-zinc fingers.

Preferably, the antibody solution composition are as follows whereby the percentage given is the percentage weight of the antibody relative to the total weight of antibody present in the solution:

1. 50% of Anti-N-glycans and 50% of Anti-O-glycans.
2. 25% of Anti-heparan sulfate, 25% of Anti-chondroitin, 25% of Anti-keratan, and 25% of Anti-dermatan.
3. 37% of Anti-leucine zippers, 33% of Anti-Turn-Helix-Turn, and 30% of Anti-zinc fingers.

Alternatively, the mixture containing EBN can be sequentially treated with solutions containing a different antibody or antibodies, and separated to extract out the desired compounds sequentially.

The isolated compounds can be further hydrolysed with vegetable and food proteases at 45° C. for 1 hour at a pH of 6.5 to 9.0. The concentration of enzymes used should be at least 10 µg/mL for effective hydrolysis. Preferably, the concentration of enzyme is up to 100 µg/mL, and corn or maize terminal proteases are used. The enzymes are denatured by heating the mixture at 70° C. for 5 minutes. The enzymes precipitate out at a temperature above 55° C., hence the mixture can be filtered at a temperature above 55° C. to afford the desired compounds as a solution in the filtrate.

The solution of desired compounds is dried to give the compounds as a powder. Preferably, the compounds are dried by freeze drying or spray drying. The freeze drying is carried out by cooling the solution to a temperature between −180 to −70° C. with liquid nitrogen or dry ice, and submitting the frozen mixture to vacuum to sublime the ice. The freeze drying can be repeated if required to give a dried powdered product.

The dried powdered product can be mixed with other additives to give a food or pharmaceutical product. Alternatively, the product can be dissolved in water along with other additives.

Through the process of separating products such as chondroitin sulfate, hyaluronic acid, and keratan sulfate and their hydrolysis, an economical method is provided to supply the compounds in high purity and variable dosage to suit the purpose. The products isolated in this process is amenable to be delivered to the user in a variety of ways and methods to allow for effective and quick delivery of the compounds to the site of action. Especially with a suitable formulation, chondroitin sulfate, hyaluronic acid, and keratan sulfate can be delivered in effective and useful doses to the sites of pain and inflammation.

Examples of some possible formulations are provided where the percentage given is the weight percentage of the component relative to the total weight of the product. The EBN extract in 25 to 70% by weight is mixed with a sugar making up the remainder to 100%. A suitable sugar is dextrin or maltodextrin.

Some possible formulations are provided as follows:
1. 70% of EBN extract product and 30% maltodextrin.
2. 60% of EBN extract product and 40% maltodextrin.
3. 50% of EBN extract product and 50% maltodextrin.
4. 25% of EBN extract product and 75% maltodextrin.

The extracted product from EBN possess therapeutic or prophylactic benefits and may be used in medicine or as preventive measures. The extract may be used to improve the skin and treat various skin ailments, dehydration and inflammatory skins, boost the immune system, delay aging, promote metabolism, protect a person's visual sight, improve blood circulation, regulate blood cholesterol level, protect cardiovascular health, invigorate and renew cells, ease arthritis discomfort, balance hormone levels, reduce incidence of Inflammation, control diabetes, treat degenerative joints, degenerative skin, degenerative nervous system and the brain, and protect from kidney failure.

In Vitro Cellular Assay Results

In vitro cellular assay experiments were done to study the potential therapeutic effects of the isolated products from EBN and the results are discussed further here.

Figure 2:
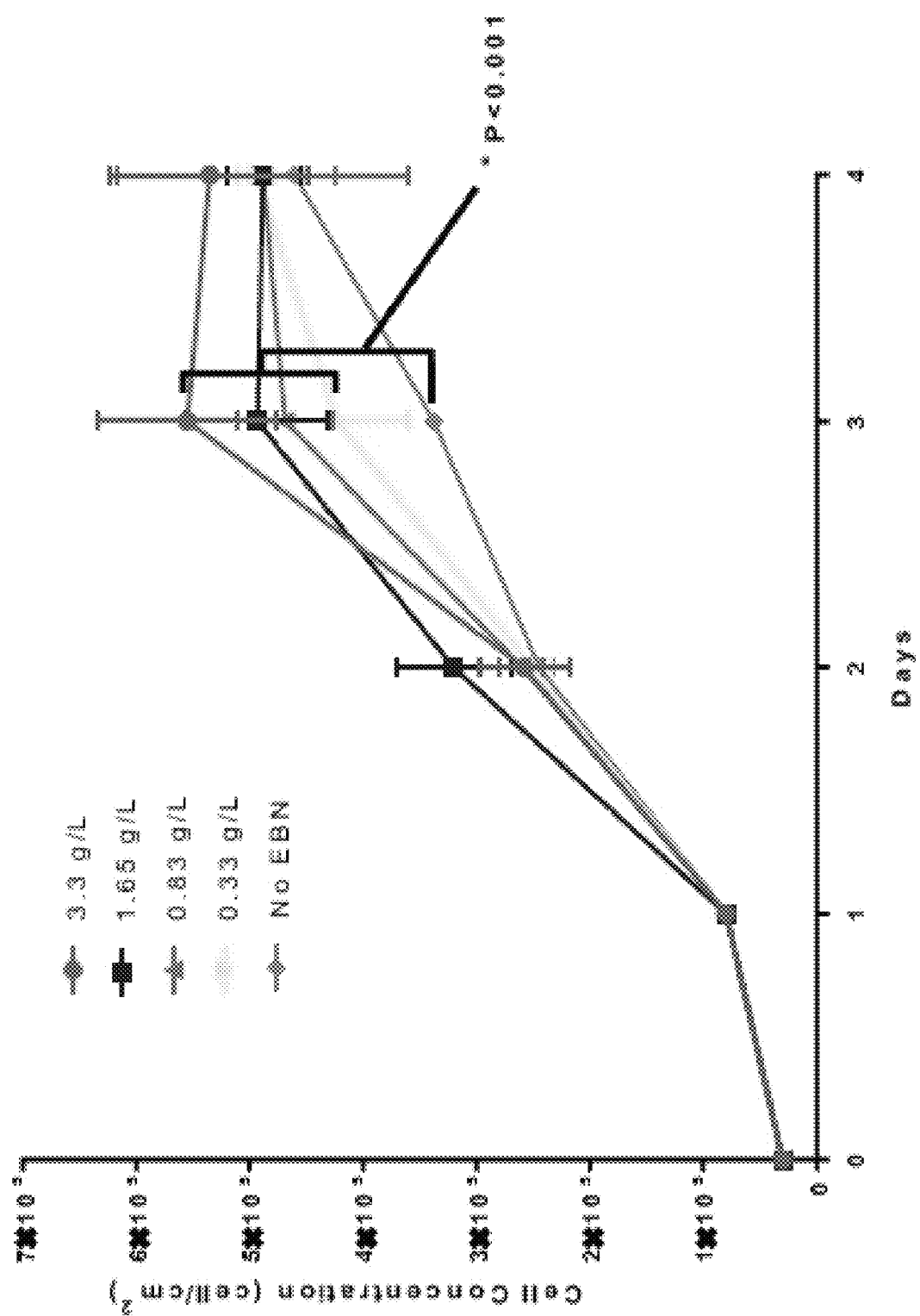
FIG. 2 Effect of SF-EBN on Vero cell growth. The presence of the SF-EBN in the culture medium showed significant improvement in cell growth (measured at day 3).

FIG. 2 shows the effect of 4 concentrations of an EBN extract product obtained from the process described using Anti-Zinc fingers on the growth of Vero cells. On Day 3, the EBN extract demonstrates that the vero cell growth is enhanced in a dose-dependent manner. Additionally, at the highest concentration (3.3 g/l) tested, the cell growth was at the maximum and significantly higher than the negative control without the addition of the EBN extract product. This indicates that the EBN product promotes Vero cell growth.

Figure 3:
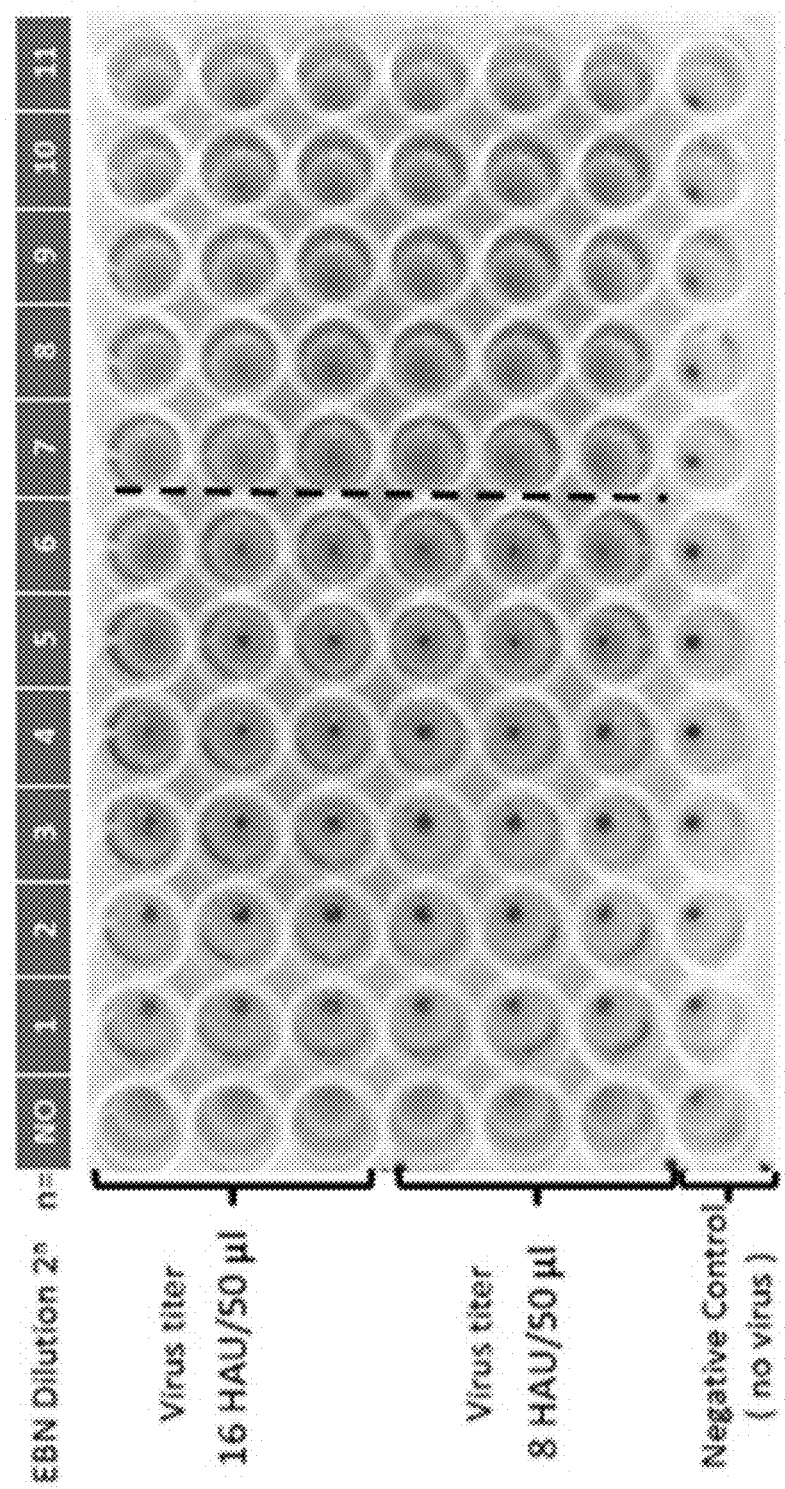
FIG. 3 SF-EBN from GeneOasis can prevent influenza virus (H1N1) mediated hemagglutination. Based on the WHO recommended virus concentration of 8HAU/50 ul, prevention of hemagglutination is obtained at SF-EBN of 0.5 g/l ($2^6$).

To determine the inhibitory effect of an EBN extract product obtained from the process described using Anti-O-glycans on the ability of haemagglutin molecules located on the surface of the influenza virus to interact with erythrocytes, a haemagglutination inhibition (HAI) assay was performed. FIG. 3 shows the results of the HAI assay for the H1N1 strain of influenza virus. Erythrocytes that do not bind with the influenza virus would settle to the bottom of the well and be observed as a red button. Erythrocytes that bind to the influenza virus would form a lattice. Haemagglutination was not observed until $2^7$ fold dilution for the two virus concentrations tested (columns 1 to 6 a dot can be seen in the well of the plate, all the columns left to the dotted line). The corresponding concentration of EBN extract at this dilution is 0.5 g/l. In other words, 0.5 g/l concentration of this EBN extract product is able to inhibit the binding of the H1N1 influenza virus to erythrocytes.

Figure 4:
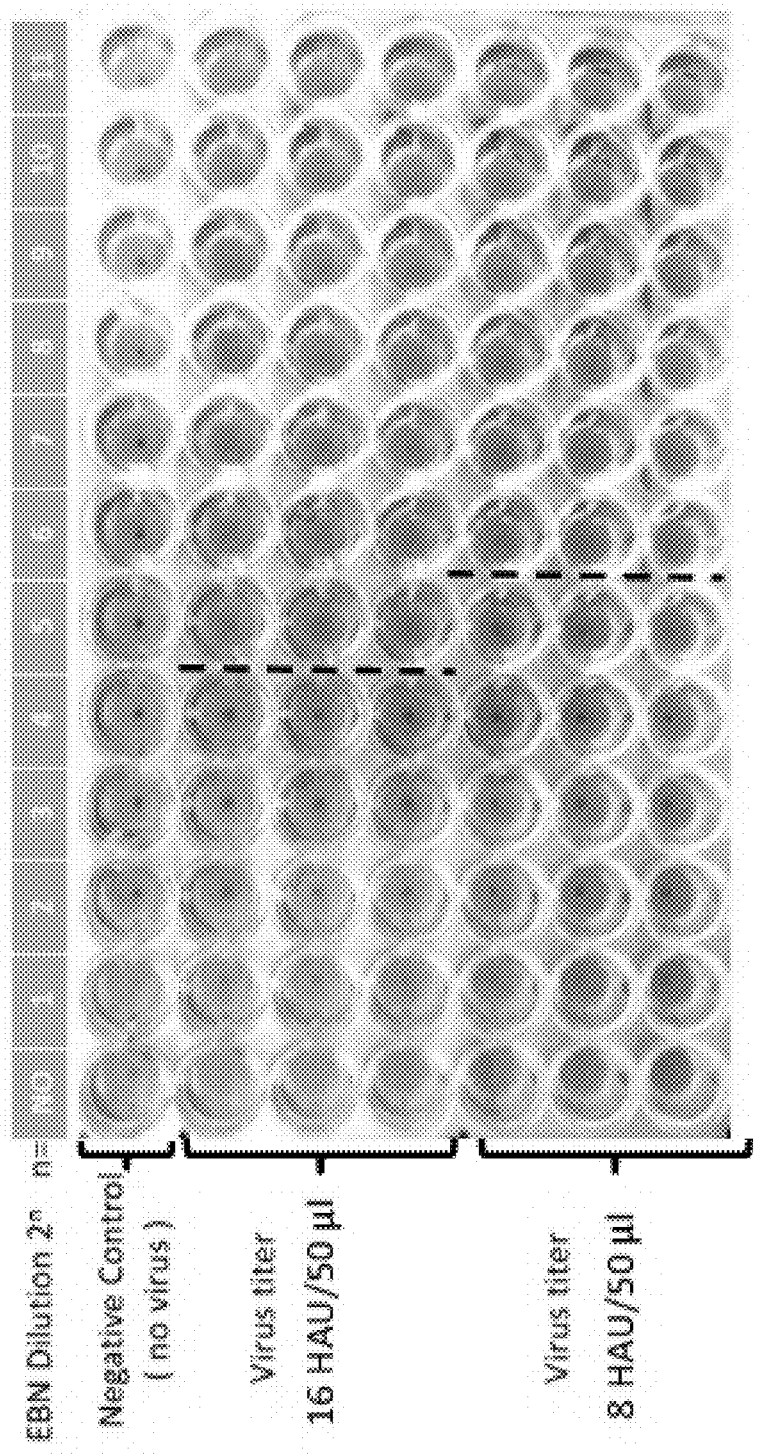
FIG. 4 Effects of SF-EBN from GeneOasis on the inhibitory effects of influenza virus (H3N2) mediated haemagglutination. Based on the WHO recommended virus concentration of 8HAU/50 ul, prevention of haemagglutination is obtained at SF-EBN concentration of 1.0 g/l (25).

FIG. 4 shows the HAI assay with the H3N2 virus strain. The concentration of EBN extract product is 2.1 g/l and 1.0 g/l at virus concentrations of 16 and 8 HAU/50 µL respectively.

Figure 5:
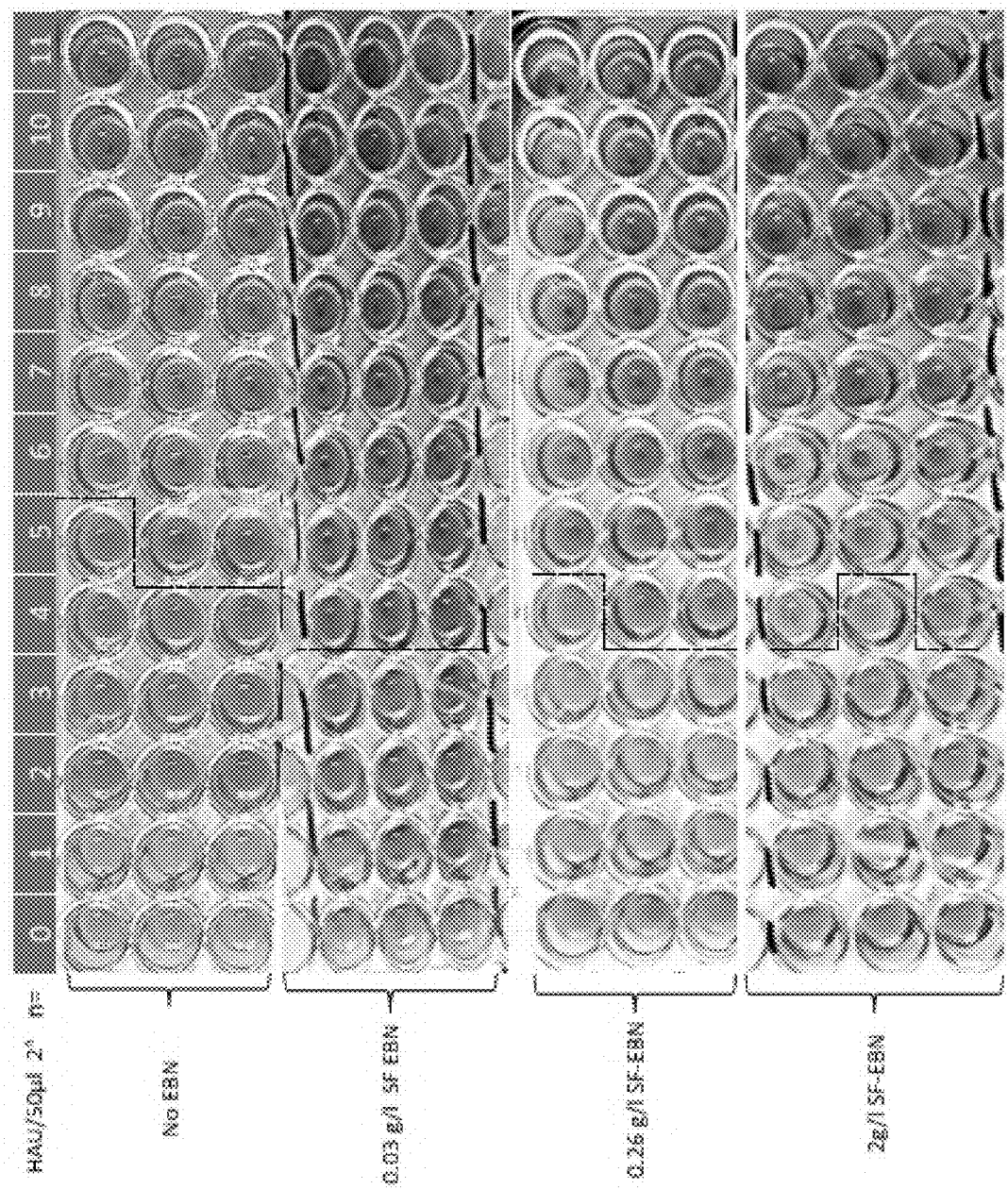
FIG. 5 Haemagglutination assay for measuring the influenza virus titer in culture supernatant after infecting Vero cells in the presence of SF-EBN. The assay was carried out 24 h post infection with H1N1 at MOI of 0.001. The dotted lines divide wells within a row where haemagglutination can be observed.

FIG. 5 shows the effect of an EBN extract product obtained from the process described using Anti-O-glycans on the inhibition of influenza virus infection of Vero cells. FIG. 5 shows the virus titer quantifications using HAI. Table 1 below shows that the EBN extract product reduce the infectivity of the H1N1 influenza virus on Vero cells.

TABLE 1

Effect of EBN extract on H1N1 virus replication in Vero cells.
Result of hemagglutination assays are derived from FIG. 5.

| Concentration of EBN extract (g/l) | Virus Titre (HAU/50 µL) | Fold reduction of infectivity |
| --- | --- | --- |
| 0 | 10.7 ± 4.6 | — |
| 0.03 | 4 ± 0 | 2.6 |
| 0.26 | 5.3 ± 2.3 | 2 |
| 2 | 5.3 ± 2.3 | 2 |

Figure 6:
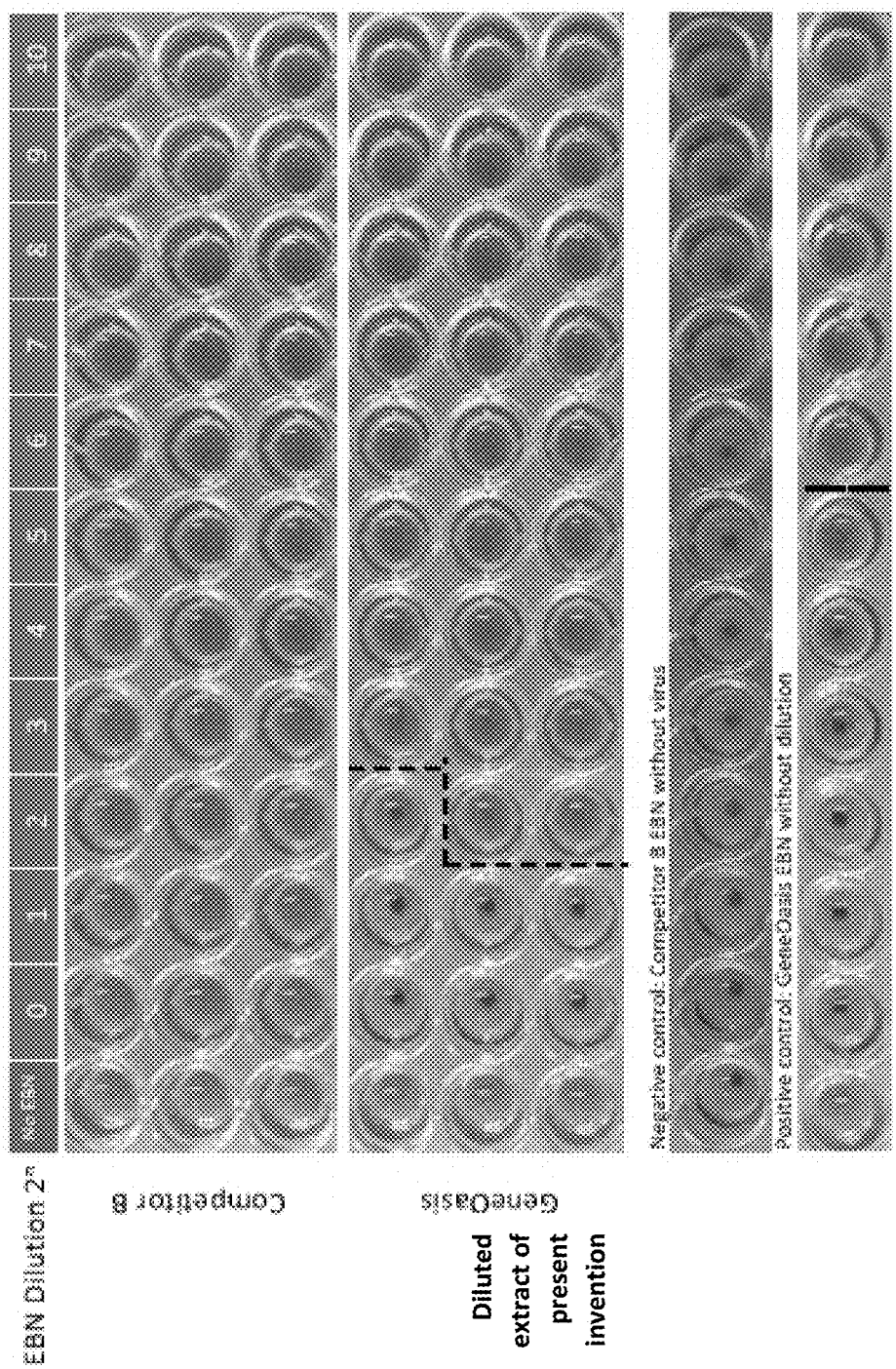
FIG. 6 Evaluation of SF-EBN from competitor B in in influenza virus (H1N1) mediated hemagglutination. H1N1 virus concentration of 16 HAU/50 ul was used. SF-EBN of the of the present invention was diluted to match the soluble protein concentrations of SF-EBN from the out any EBN extracts (0%). This shows that the present EBN extracts can elicit a statistically significant increase in human stem cell proliferation during the course of chondrogenic differentiation in vitro. This is novel as this is the first study to show not only an increase but also a statistically significant increase in DNA (cellular proliferation). Increase in DNA content is commonly used as a measure of cellular proliferation. Statistical analysis was performed with ordinary one-way ANOVA with Tukey's multiple comparisons test. Blue boxes highlight those that can be potentially significant if analysis can be done on more samples. Red boxes highlight those that are statistically significant. p values, * $p<0.05$.

The effect of the EBN extract product obtained from the process described using Anti-O-glycans on the inhibition of H1N1 viral activity were compared to two commercially available EBN solutions (Competitor A and B). The soluble protein content in the EBN extract solution, competitor A and B was determined by DC™ protein assay (Bio-Rad, Cat. No. 5000116) with bovine serum albumin as the protein standard. The soluble protein content of the three solutions were determined to be 2021 µg/mL, 823 µg/mL and 628 µg/mL respectively (Table 3). Hence, the EBN extract solution obtained from the process was diluted to match the respective competitor solution. However, competitor A EBN solution was found to be cytotoxic to the cells and was not tested further, while competitor B EBN solution showed no inhibition of the H1N1 virus. Thus FIG. 6 shows the comparison of the EBN extract solution of the present invention against competitor B's EBN solution.

TABLE 3

Physical properties of EBN solutions from competitor A and B.

| | Soluble Protein Content (µg/ml) | Osmolarity (mmol/kg) | Turbidity ($OD_{600}$) | pH |
| --- | --- | --- | --- | --- |
| GeneOasis | 2021 | 348 | 0.067 | 8.6 |
| Competitor A | 823 | 187 | 0.056 | 6.7 |
| Competitor B | 628 | 220 | 0.056 | 7.3 |

Figure 7:
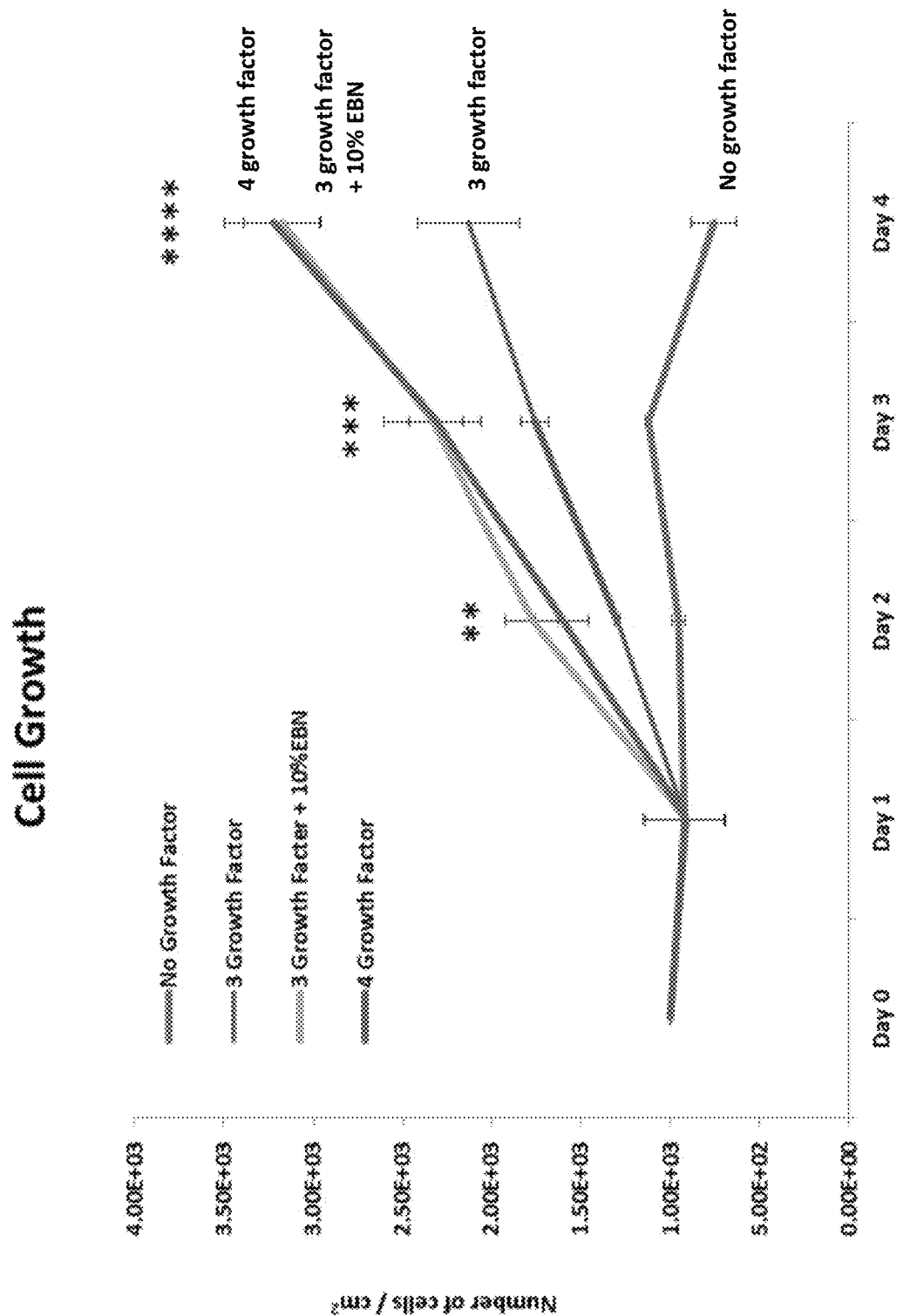

FIG. 7 shows the effect of an EBN extract product obtained from the process described using Anti-N-glycans and/or Anti-Helix-Turn-Helix on human stem cell proliferation during cell expansion. The data in FIG. 7 shows that the combination of 10% EBN extract and 3 growth factors have a similar positive effect on human stem cell proliferation as using 4 growth factors. The 10% EBN can only replace the epidermal growth factor (EGF) and act as a substitute for EGF. EGF is not available as a food supplement and Pan et al. (Environ. Health Perspect., DOI: 10.1289/ehp1409200) has shown that human EGF and parabens may lead to increase proliferation of breast cancer cell lines. Therefore, an EBN extract would be a viable substitute for individuals who do not produce endogenous EGF needed for human mesenchymal stem cells (hMSC) activation and differentiation to chondrocytes.

Figure 8:
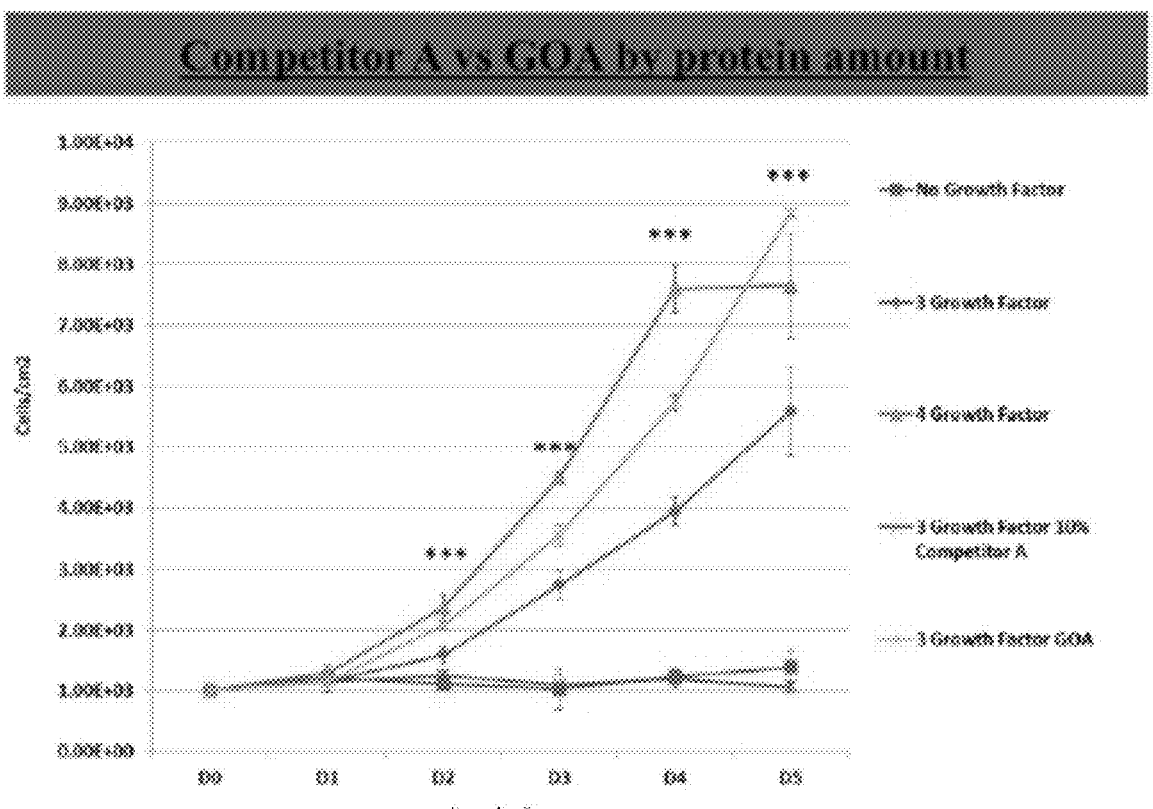
Figure 8:
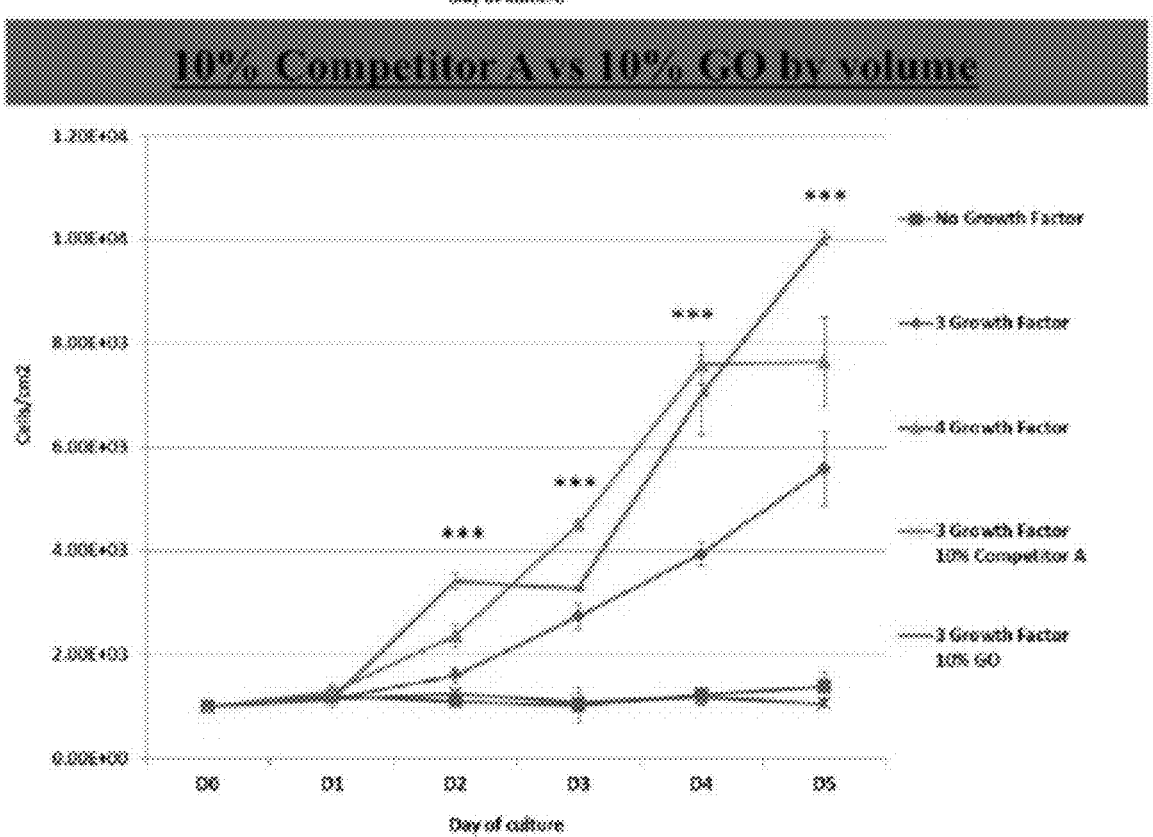
Figure 9:
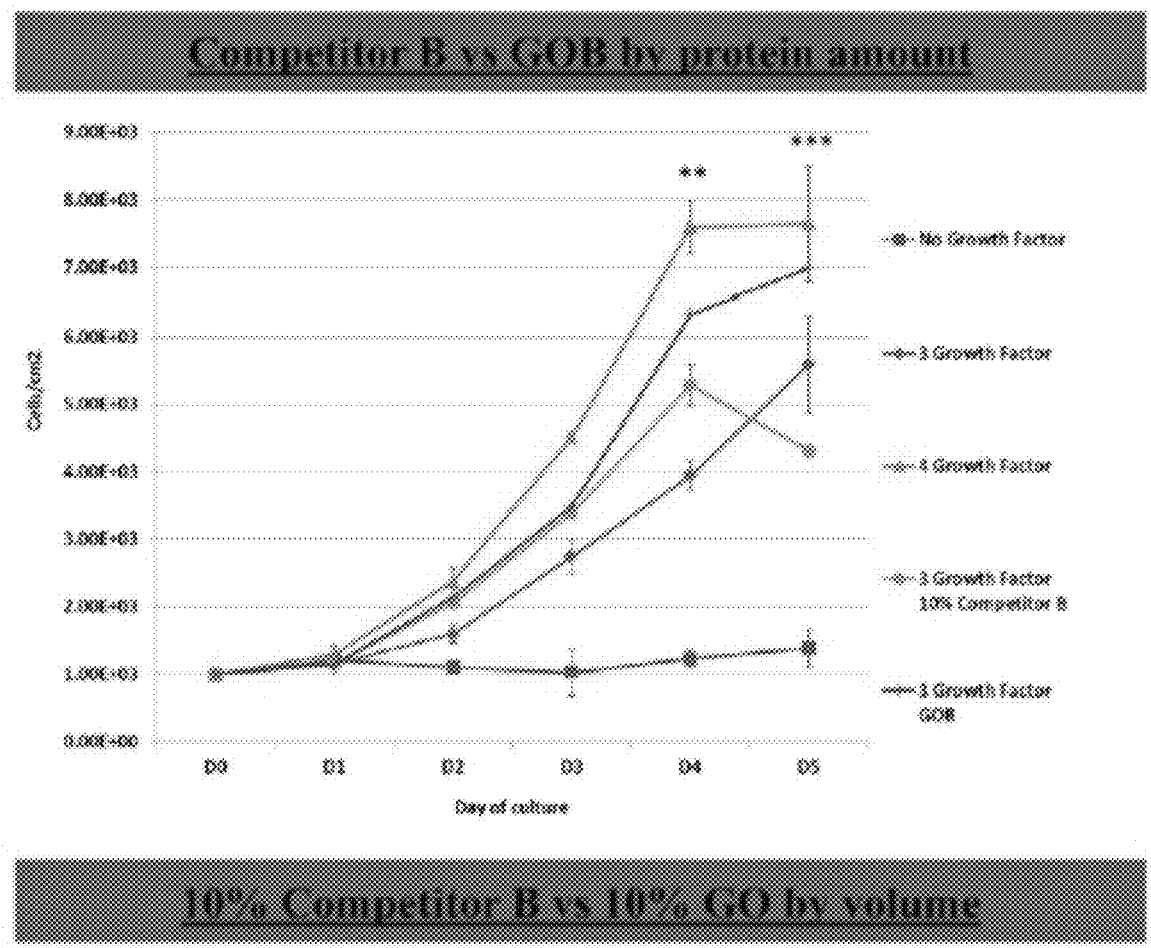
Figure 9:
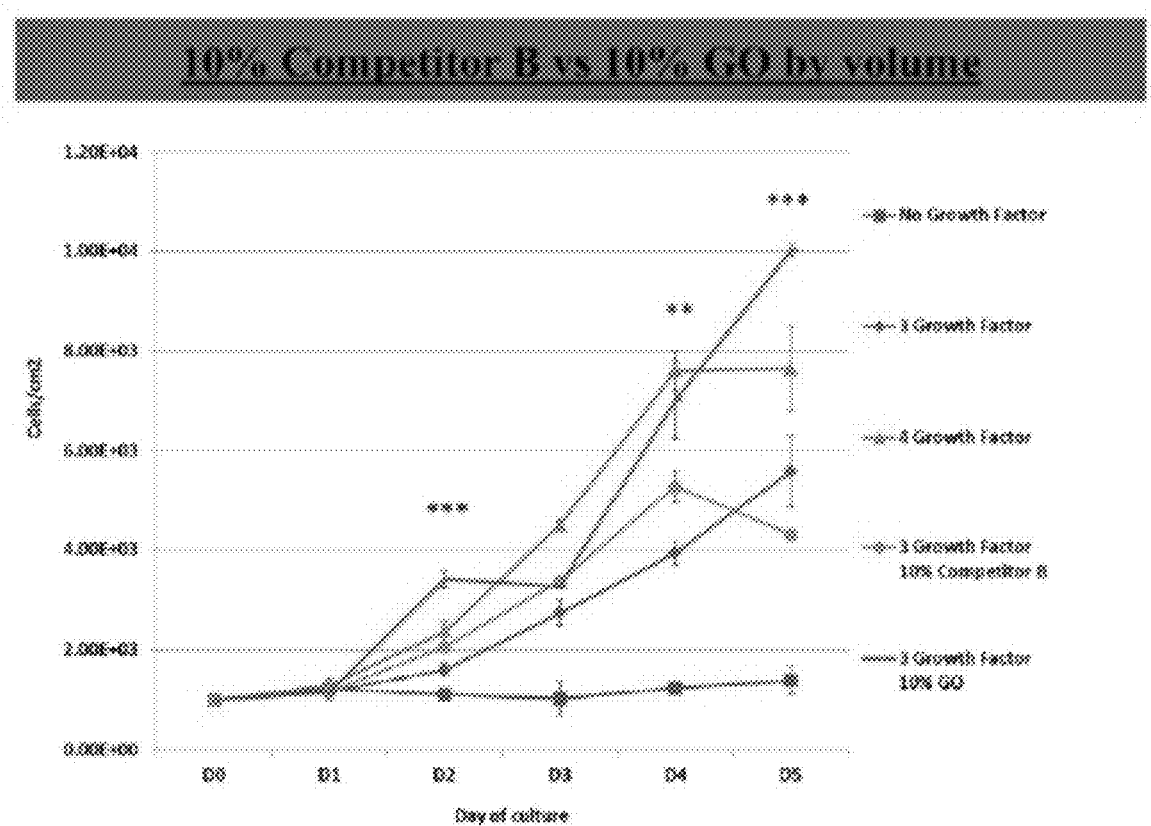

FIGS. 8 and 9 shows a comparison between an EBN extract product obtained from the process described using Anti-N-glycans and/or Anti-Helix-Turn-Helix on human stem cell proliferation compared to an EBN extract from competitor A and B. The effect of the EBN extract to replace EGF is much more significant for the EBN extract compared to both competitor A and B products.

Effect of EBN's Extract on Influenza
Materials and Methods
1. Extraction Method

With reference to FIG. 1, a piece of EBN weighing 10-50 g was washed in an enzymatic solution to remove mites for 5 minutes, the solution was removed. The bird's nest was washed with an aqueous solution containing nitrite reductase, the solution was removed. The cleaned EBN was dried for 12 h at 70° C. The dried and cleaned EBN was grounded and sifted through a mesh (600 µm pore size) to remove plume and foreign substances. The grounded EBN was kept in distilled water (25 g/1000 ml water) at 5° C. for 5 h and then heated at 121° C. for 10 min for sterilization.

The suspension was mixed with 270 ml of a solution containing an antibody for 20 min, and followed by 200 ml of acid at 4° C. overnight. The extract was homogenized with a homogenizer and heated at 100° C. After cooling to room temperature, the solution pH was adjusted to 7.0 by dropwise addition of an alkali with stirring. The antibody bounded compounds were released from the antibody by adding excess larger peptides of natural glycoaminoglycans and cellular transcriptional regulators. The released compounds are subsequently isolated from the added peptides, enzymes and antibodies via the use of a dialysis bag.

The extract was treated with a corn or maize terminal protease at 45° C. for 1 hour at a pH of 6.5-9.0. The enzyme was inactivated by heating the suspension to 70° C. for 5 min, and filtering off the precipitated enzyme at a temperature above 55° C. The isolated products in the filtrate was freeze dried for at least 24 hours.

For in vitro assays testing, the respective freeze dried EBN powder was dissolved in distilled water to prepare a stock solution with a concentration of 33.3 g/l and sterilized by gamma-radiation at 25 kGry for 1 hour. Any insoluble matter was removed via centrifugation at 8000 RPM. The stock solution was stored at −20° C. until required.

Soluble protein concentration in SF-EBN was determined by DC™ protein assay (Bio-Rad, Cat. No. 5000116) and used bovine serum albumin as the protein standard. Osmolarity and turbidity was measured by a vapor pressure osmometer (VAPRO) and microplate reader (Tecan Infinite M200) respectively.

In an alternative method, the bird's nests were washed for 10 min and dried for 12 h at 70° C. The dry bird's nests were ground and sifted through a mesh (600 µm pore size) to remove plume and foreign substances. The grounded bird's nests kept in distilled water (25 g/1000 ml water) at 5° C. for 5 h and then heated at 121° C. for 10 min (sterilization). The suspension was mixed with 270 ml of the extraction solution for 20 min and followed by 200 ml of acid at 4° C. overnight. The extract was homogenized with a homogenizer and heated at 100° C.

After cooling to the room temperature, the solution pH was adjusted to 7.0 by dropwise addition of an alkali while stirring. The extract was treated with the proprietary enzyme (the concentration depends on enzyme specifications) at 45° C. for 1 hour at pH 6.5-9.0. The enzyme was later inactivated by heating the suspension to 70° C. for 5 min. The treated extract was freeze dry. For in vitro assays testing, the freeze dried EBN powder was dissolved in distilled water at concentrations of 33.3 g/l and sterilized by gamma-radiation at 25 kGry for 1 hour. The insoluble EBN extract was removed via centrifugation at 8000 RPM. The soluble fraction (SF-EBN) stored in −20° C. was used for influenza neutralization studies.

Soluble protein concentration in SF-EBN was determined by DC™ protein assay (Bio-Rad, Cat. No. 5000116) and used bovine serum albumin as the protein standard. Osmolarity and turbidity was measured by a vapor pressure osmometer (VAPRO) and microplate reader (Tecan Infinite M200) respectively 2. Expansion and Creation of Vero Cell Bank Vero cells (ATCC CCL-81) from a master cell bank at Passage 129 were thawed and expanded in serum-free media, OptiPro serum free medium (Life Technologies, Cat. No. 12309-019) supplemented with 4 mM L-glutamine (Life Technologies, Cat. No. 25030149) to generate a working cell bank with 20 vials of 2×106 cells per vial. Vero cells were passaged every 4 days using StemProAccutase (Life Technologies, Cat. No. A11105-01) for cell detachment and single cells generated were inoculated at cell density of 1.5×104 cells/cm$^2$.

3. Effect of EBN Extract Solution on Vero Cell Growth

To test the effect of SF-EBN on cell growth, Vero cells were seeded at 3×104 cells/well in 24-well tissue culture plate in OptiPro serum free medium. One day post seeding, SF-EBN (33.3 g/l) was added to respective wells to attain final concentrations of 3.3 g/l (10% v/v), 1.65 g/l (5% v/v), 0.83 g/l (2.5% v/v), and 0.33 g/l (1% v/v). Cell growth was monitored daily over 4 days. Cell counts were performed using Nucleocounter NC-3000 (Chemometec, Inc.) according to the recommended protocol.

4. Influenza Virus Propagation in Vero Cells

Vero cells were seeded at 2.5×104 cells/cm2 to obtain sub-confluence after 2 days of culture were infected with influenza A H1N1 virus (IVR-116, NIBSC code 06/108) and H3N2 (A/Wisconsin/67/2005 HGR, NIBSC code 06/112)) at MOI (multiplicity of infection) of 0.001 to 0.01. Porcine trypsin (Sigma-Aldrich, Cat. No. T5266, 1500 BAEE unit/mg) used for the activation of influenza virus was prepared with deionized water and filter sterilized to make a stock concentration of 5 mg/ml. During the virus amplification, trypsin was added 30 minutes after inoculation with the virus to obtain a final concentration of 5 µg/ml. Virus containing culture supernatant was harvested 2-3 days later (when 80% cytopathic effect (CPE) was observed) and centrifuged to remove cell debris. The virus stock solutions (H1N1 and H3N2) were stored in −80° C. Their virus titers were quantified using haemagglutination and tissue culture infectious dose (TCID50) assays as described below.

5. Quantification of Influenza Virus Titers

Virus titers were quantified using the haemagglutination assay and tissue culture infectious dose (TCID50) assay as described in Chen et al. (BMC Biotechnol., 2011, 11-81). For the haemagglutination assay, 4% human erythrocytes (Siemens Healthcare Diagnostics) were diluted in Dulbecco's phosphate buffer solution (DPBS, Life Technologies, Cat. No. 14190-250) to obtain a 0.75% cell suspension. The diluted erythrocyte suspension was then added to 2-fold serial dilutions of virus and control samples. The highest dilution of virus which causes complete haemagglutination of erythrocytes is considered the HA titration end point. The HA titer (HAU/50 µl) is the reciprocal of the dilution of virus in the last well with complete haemagglutination (E.g. A dilution of $2^7$ gives haemagglutination unit (HAU/50 µl) of 128).

TCID50 assay was performed in triplicates by adding 10-fold serially diluted virus samples to Vero cells cultivated in 96-well plates using OptiPro serum free medium supplemented with 5 µg/ml of porcine trypsin. The plates were incubated for 3 days at 37° C. in a 5% CO2 atmosphere and then the cultures were checked under a light microscope for cytopathic effect. The dilution of the suspension that causes cytopathic effects in 50% of the cultures (the median tissue culture infective dose, TCID50/ml) was calculated according to the formula of Reed and Muench (1938).

6. Haemagglutination Inhibition Assay

Haemagglutination inhibition (HAI) assay was carried out using 96-well microtiter plates as described previously (Guo et al., 2006, Antiviral Res., 70, 140-146). DPBS containing Mg2+ and Ca2+ was used as a dilution buffer. Human erythrocytes were used as indicator cells. Virus suspension (8 HAU/50 µl in 0.05 ml DPBS and 16 HAU/50 µl in 0.05 ml DPBS respectively) was added to each well containing the EBN solution in twofold serial dilutions with the dilution buffer. 0.05 ml of 0.75% (v/v) human type 0 erythrocytes in DPBS was added to the plates and incubated for 1 h at 4° C. The maximum dilution of the samples showing complete inhibition of haemagglutination was defined as the HAI titer of the EBN solution.

7. Effect of EBN on Inhibition of Influenza Virus Replication

Vero cells were cultured in T25 flasks in OptiPro serum free medium with seeding density of 3×10$^4$ cells/cm$^2$. When cell culture reached 90% confluency, the cultures were infected with influenza virus at MOI of 0.001. SF-EBN was then added to reach final concentrations of 2 g/l (6.25% v/v), 0.26 g/l (0.78% v/v) and 0.03 g/l (0.10% v/v). After 2 h, SF-EBN containing culture medium was removed. The cells were washed three times with OptiPro serum free medium. Porcine trypsin were added to obtain a final concentration of 5 µg/ml. Culture supernatant were collected after 24 h. SF-EBN antiinfluenza effect was validated via haemagglutination and TCID50 assays.

8. Human Mesenchymal Stem Cells (hMSC) Cell Culture hMSC (passage 8 to 9) were plated at a density of 2400 to 2800 cells/cm$^2$ in either T175 cm$^2$ cell culture flasks or Nunc™ EasyFill™ Cell Factory™ Systems in MSC growth medium consisting of Minimum Essential Medium a, 10% Fetal Bovine Serum (FBS) and 1% Penicillin-Streptomycin (all from Gibco). The medium was changed every 2 to 3 days. hMSC were passaged at about 70% confluency when they were harvested using 0.25% Trypsin-EDTA (Gibco) for 5 mins at 37° C. Viability and cell count assays were performed with the automated NucleoCounter® NC-3000 (Chemometec). All cultures were maintained at 37° C. in a 5% $CO_2$ humidified incubator (Thermo Scientific).

9. hMSC Cell Expansion for Cell Growth Curve hMSC were plated at a density of 1000 cells/cm$^2$ in Nunclon™ Delta Surface 24-well plates. hMSC was seeded at day 0 and cultured for 4 days. hMSC grown only in BTI's proprietary serum-free MSC growth medium without any growth factors and GeneOasis Pte Ltd's EBN extracts were used as negative controls, and were known as "No Growth Factors". hMSC grown in BTI's proprietary serum-free MSC growth medium supplemented with 10 ng/ml of PDGF (Peprotech), 5 ng/ml of TGFβ-1 (Peprotech), and 10 ng/ml of FGFβ (Gibco) were also used as negative control, also referred to as "3 Growth Factors". hMSC grown in BTI's proprietary serum-free MSC growth medium supplemented with 10 ng/ml of PDGF (Peprotech), 5 ng/ml of TGFβ-1 (Peprotech), 1 ng/ml of EGF (Peprotech) and 10 ng/ml of FGFβ (Gibco) were used as positive control, also referred to as "4 Growth Factors". hMSC grown in serum-free MSC growth medium supplemented with 3 growth factors (excluding EGF) with 10% EBN (vol/vol) were tested and was referred to as "3 Growth Factors+10% EBN". 10% (vol/vol) EBN was added on day 1. Cell count assays were performed daily with triplicates for each condition with the automated NucleoCounter® NC-3000 (Chemometec). All cultures were maintained at 37° C. in a 5% CO2 humidified incubator (Thermo Scientific).

10. Chondrogenic Differentiation hMSC were grown as micromass pellets in clear round bottom ultra-low attachment 96 well plates (Corning) for chondrogenic differentiation. Pellets were formed by centrifugation at 1000 rpm for 5 mins at room temperature (rt) using $2\times10^5$ hMSC per pellet per well. They were cultured in chondrogenic differentiation medium containing DMEM-high glucose (Gibco), 1 mM sodium pyruvate (Gibco), 100 nM dexamethasone (Sigma), 0.1 mM L-ascorbic acid-2-phosphate (Sigma), 1% ITS+1 (Sigma), L-proline (Sigma) and 1% Penicillin/Streptomycin (Gibco). Pellets grown only in chondrogenic differentiation medium without EBN extracts were used as negative controls. Pellets grown in chondrogenic differentiation medium with different concentrations of EBN (1.25%, 2.5%, 5% and 10% vol/vol) were tested. Pellets grown in chondrogenic differentiation medium supplemented with 100 ng/ml of BMP2 were used as positive controls. Chondrogenic medium with or without supplementation was changed every 2 to 3 days.

11. DNA, GAG and Collagen II Content Evaluation

Pellets (at least 3 per condition per timepoint) were rinsed once with Phosphate Buffer Saline (PBS) before immediate storage at $-80°$ C. After thawing, the pellets were either digested with 0.125 mg/ml papain at 65° C. overnight for DNA and GAG quantification, or with 0.1 mg/ml pepsin at 4° C. over 2 nights followed by 0.1 mg/ml elastase digestion at 4° C. overnight for Collagen II evaluation. DNA quantification was done using Quant-iT Picogreen dsDNA Assay, GAG measurement was done using Blyscan Sulfated Glycosaminoglycan Assay (Biocolor), and Collagen II quantification was done by ELISA against Type II Collagen (Chondrex), all in accordance with manufacturer's instructions. All fluorometric and optical readings were taken with a Tecan Infinite M200.

12. Statistical Analyses

Data were analyzed with statistical software Prism 6 (GraphPad). Multiple comparisons among different conditions were compared statistically using ordinary one-way analysis of variance (ANOVA) with Tukey's multiple comparisons test. For all statistical tests, p values less than 0.05 were considered significant.

13. Comparison of GeneOasis EBN with Competitor A EBN and Competitor B EBN hMSC were grown in a similar fashion as detailed in part 9. hMSC was seeded at day 0 and cultured for 5 days. 2 types of comparison of the EBN extract to either Competitor A EBN or Competitor B EBN were performed. One type of comparison was to compare 10% of competitor EBN to GeneOasis EBN by normalizing or controlling for protein content (i.e. GeneOasis EBN control would have same amount of protein as that of the respective competitor). As measured, 10% of Competitor A EBN is equivalent to 4.39% of GeneOasis EBN. Thus, MSC growth medium supplemented with 3 growth factors (excluding EGF) with 4.39% GeneOasis EBN (vol/vol) were tested and was referred to as "GOA". MSC growth medium supplemented with 3 growth factors (excluding EGF) with 10% EBN of Competitor A (vol/vol) were tested and was referred to as "3 Growth Factors+10% Competitor A". Likewise for Competitor B, 10% of Competitor B EBN is equivalent to 3.35% of GeneOasis EBN. Thus, MSC growth medium supplemented with 3 growth factors (excluding EGF) with 3.35% GeneOasis EBN (vol/vol) were tested and was referred to as "GOB". MSC growth medium supplemented with 3 growth factors (excluding EGF) with 10% EBN of Competitor B (vol/vol) were tested and was referred to as "3 Growth Factors+10% Competitor B". The second type of comparison was to compare 10% of competitor EBN to GeneOasis EBN by normalizing or controlling for volume (i.e. 10% GeneOasis EBN would be compared to 10% of Competitor EBN by volume). The investigators are blinded to the identity of Competitor A and B throughout the execution and data analysis of the related experiments.

In summary, we describe the novel EBN extraction method and found that the EBN extract of the present invention could inhibit the haemagglutination of influenza A to human erythrocyte and reduce infectivity in Vero cells. Using soluble fraction of EBN extract (SF-EBN), we showed that at the minimal concentrations of 0.5 g/l and 1 g/L EBN could inhibit haemagglutination for H1N1 and H3N2 respectively. For the in vitro infectivity of influenza H1N1, we show that the addition of SF-EBN at concentrations of between 0.03 to 2 g/l to the Vero cell culture reduced the virus titer generated by at least 2 fold when compared to the culture without SF-EBN supplementation. Commercial EBN solutions were also tested in the haemagglutination inhibition assay with influenza A. These EBN solutions were found to be either cytotoxic to the cells or did not exhibit any detectable anti influenza virus activity. In conclusion, GeneOasis' proprietary EBN extract is potent and superior in the prevention of influenza virus infection.

Results

Prior to testing the effect of SF-EBN on cells and influenza virus replication, we have carried out soluble protein assay with bovine serum as the standard as shown in Table 1 below. This will provide the reference point for future comparison between various sources and extraction methods of EBN.

TABLE 1

Properties of SF-EBN

| Properties | |
|---|---|
| Soluble protein content | 2021 µg/mL |
| Osmolarity | 348 mmol/kg |
| Turbidity | $OD_{600}$ 0.067 |
| pH | 8.6 |

Effect of EBN on Vero Cell Growth

Four SF-EBN concentrations (3.3 g/l (10% v/v), 1.65 g/l (5% v/v), 0.83 g/l (2.5% v/v), and 0.33 g/l (1% v/v)) were tested for their effect on Vero cell growth in tissue culture plates. As shown in FIG. 2, SF-EBN enhanced Vero cell growth in a concentration dependent manner when compared to the control without SF-EBN. In the presence of 3.3 g/l SF-EBN, Vero cells reached the confluent cell density on day 3 ($\sim5\times105$ cells/cm2) earlier than the control (Day 4). The growth enhancement can be related to the presence of EGF-like molecules found in EBN extract, where EGF is the known essential growth factor required by Vero cells for growth.

Inhibitory Effect of EBN Extract on Influenza Virus Infection

To determine the inhibitory effect of SF-EBN on the ability of the haemagglutinin molecules located on the surface of the influenza virus to interact with erythrocytes, we have carried out haemagglutination inhibition (HAI) assay, a commonly used assay for quantitating of the concentration of influenza viruses. Two virus concentrations of 16 and 8 HAU/50 µl were prepared, (8 HAU/50 µl is the recommended concentration found in WHO laboratory procedure for serological detection of influenza virus). As shown in FIG. 3, twofold serial dilutions of the SF-EBN (column 2-12) were mixed with human erythrocytes before the addition of influenza viruses at two concentrations 16 and 8 HAU/50 µl (mentioned above) in a 96-well plate. Erythrocytes that do not bind with influenza virus would settle to the bottom of a well and form a red button. In the case that the viruses bind to erythrocytes, a lattice was formed. Haemagglutination was not observed until 27 fold dilution for the two influenza virus concentrations tested. The corresponding SF-EBN concentration at that dilution is 0.5 g/l. This indicates that at this concentration of 0.5 g/l (but not lower) EBN blocks haemagglutination. The experiment was repeated using influenza H3N2 as shown in FIG. 4. Higher SF-EBN concentrations of 2.1 g/L and 1.0 g/L were required to block haemagglutination in the presence of H3N2 virus at concentrations of 16 and 8 HAU/50 µl respectively. These results demonstrate that EBN extract can compete with the viral hemagglutinin molecules (measured by haemagglutination of human erythrocytes) to reduce influenza virus infectivity (similar to the activity of specific antiserum).

We also investigated the effect of SF-EBN on the inhibition of influenza virus infection of Vero cells. Confluent Vero cells were infected with influenza virus H1N1 (M01 of 0.001) in the presence of SF-EBN of 2 g/l, 0.26 g/l and 0.03 g/l. After 24 h post infection, the culture supernatants were collected for virus titers quantification using haemagglutination assay. As shown in Table 2 below, SF-EBN concentration of between 0.03 to 2 g/l showed about a twofold reduction in H1N1 virus titer. This indicates that EBN extract can reduce infectivity of influenza virus (using Vero cells).

TABLE 2

Effect of SF-EBN on influenza virus H1N1 replication in Vero cells.

| SF-EBN (g/l) | Virus Titre (HAU/50 µl)[#] | Fold reduction |
| --- | --- | --- |
| 0 | 10.7 ± 4.6 | — |
| 0.03 | 4 ± 0 | 2.6 |
| 0.26 | 5.3 ± 2.3 | 2 |
| 2 | 5.3 ± 2.3 | 2 |

[#]Result of hemagglutination assays are derived from FIG. 5
Evaluation of SF-EBN from competitors for anti-viral effect Two commercially available EBN solutions (Competitor A and B) were selected for anti-viral activity determination. As shown in Table 3 below, these commercial EBN solutions exhibited lower soluble protein concentration and osmolarity than SF-EBN.

TABLE 3

Physical properties of EBN solutions from competitor A and B.

| | Soluble Protein Concent (µg/ml) | Osmolarity (mmol/kg) | Turbidity ($OD_{600}$) | pH |
| --- | --- | --- | --- | --- |
| GeneOasis | 2021 | 348 | 0.067 | 8.6 |
| Competitor A | 823 | 187 | 0.056 | 6.7 |
| Competitor B | 628 | 220 | 0.056 | 7.3 |

Hence, SF-EBN was diluted with water to match the soluble protein concentration of the commercial EBN solutions for the haemagglutination assay. Competitor A EBN solution was excluded from the assay as it was found to be cytotoxic to the cells, whereas the other EBN solutions (competitor B) showed no growth inhibition effect. The result of the haemagglutination assay is shown in FIG. 6. We found that the commercial EBN solution (competitor B) did not exhibit any activity in preventing H1N1 virus mediated haemagglutination of erythrocytes. This indicates this commercial EBN solution has no anti-viral properties as shown with SF-EBN. Since EBN is known to have anti-influenza virus activity, we can conclude that the novel method for EBN extraction developed by geniuses to be superior in the preservation of the antiviral property.

Effect of EBN's Extract on Human Neural Progenitor Cell Growth and Differentiation
1. Material and Methods
1.1 Derivation and Maintenance of Human Neural Progenitors Human neural progenitors (hNPC) were generated from human embryonic stem cell line (hESC) HES-3 by using the microcarrier suspension cultures. Subsequently, hNPCs were then grown on geltrex-coated plates, and fed with NPC medium (Neurobasal Medium, 1×NEAA, 1× Penicillin-Streptomycin, 2 mM L-Glutamine, 1× N2, 1× B27 minus Vitamin A, all from Life Technologies) supplemented with EGF (20 ng/ml, Peprotech) and FGF (20 ng/ml, Peprotech). The medium was changed every other day. hNPCs were passaged using StemPro Accutase (Life Technologies) when cells reached about 80-90% confluency.

1.2 Cell Growth and Cell Count of Human Neural Progenitors hNPC were plated at a density of 2000 cells/well in geltrex-coated 48-well plates, and grown for 1 week. hNPCs were fed with NPC medium supplemented with different combinations of growth factors (EGF, FGF) and GeneOasis Pte Ltd's EBN extracts. Cells were then lysed for total and viable cell count using a nuclei count method with DAPI by NucleoCounter NC3000 (Chemometec) according to the manufacturer's instructions.

1.3 Cell Proliferation and Differentiation of Human Neural Progenitors hNPC were plated at a density of 150,000 cells/well in geltrex-coated 6-well plates, and grown for 1 and 3 weeks. hNPCs were fed with NPC medium supplemented with different combinations of growth factors (EGF, FGF) and GeneOasis Pte Ltd's EBN extracts. During the culture period, hNPCs were passaged when cells reached 80% confluency. By the time point (1st week and 3rd week), hNPCs were dissociated into single cells with Tryple (Life Technologies). Subsequently, cells were fixed, permeabilized, and incubated with primary antibodies, Anti-Ki-67 (1:200, BD Bioscience) for cell proliferation and anti-Tubulin R 3 (1:1000, Covance) for Neuron differentiation assessments. Alexa Fluor 488° goat antimouse (Life Technologies) was used as the secondary antibody. All incubations were conducted at 4° C. for 20 min. Fluorescent measurements were done using flow cytometer (GUAVA, Millipore). FlowJo software is used for the analysis of flow cytometry data.

2. Results

Figure 10A:
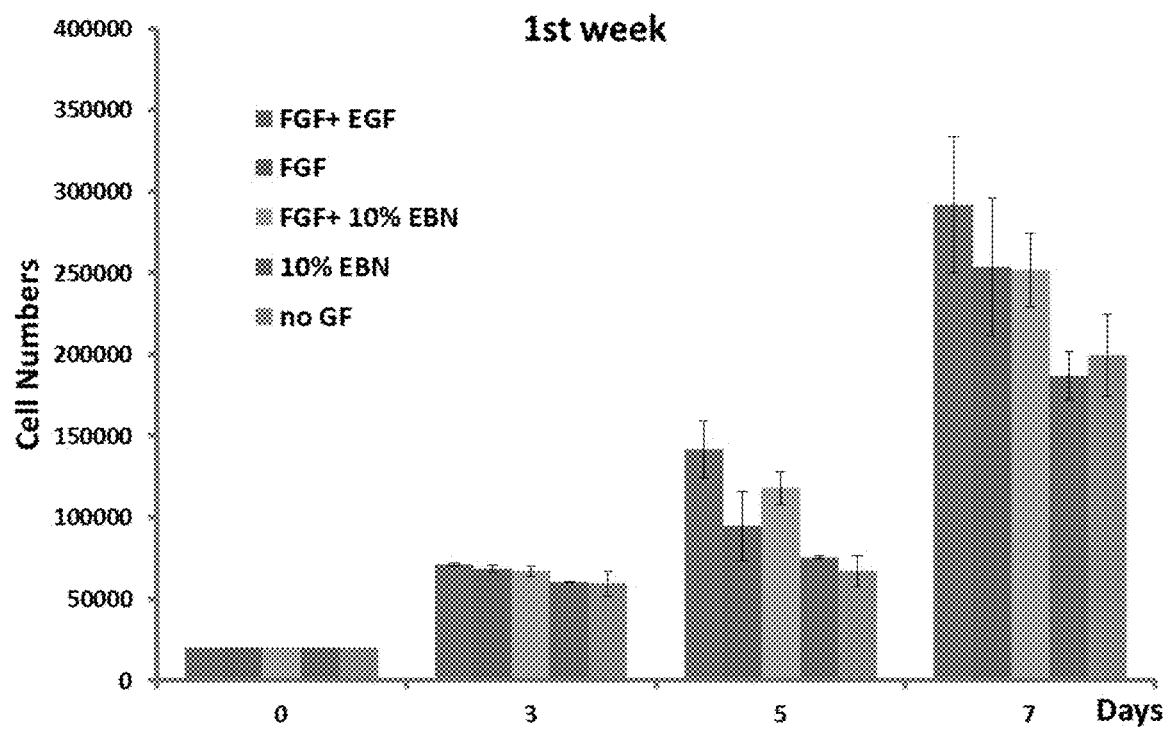

In this study, we investigated whether EBN extract can support the expansion of hNPCs derived from human embryonic stem cells (hESCs). As shown in FIG. 10, hNPCs cultured in the presence of FGF-2 and EGF exhibited highest cell yield after 7 days. EBN extracts combined with growth factor FGF-2 achieved comparable cell growth profiles as those with FGF-2+EGF and FGF-2 alone conditions. Adding EBN without FGF-2 has resulted in lower cell growth. The results suggested that the EBN extract cannot replace the FGF2, which is the most critical growth factor for hNPC proliferation. On the other hand, even though EBN contained EGF-like activities, which was shown in the report describing the effect of EBN extract on proliferation of human mesenchymal stem cells in serum free medium, we observed no beneficial effect of EBN extract in the short term expansion of hNPCs in the presence of FGF-2.

Fetal Bovine Serum (FBS) and 1% Penicillin-Streptomycin (all from Gibco). The medium was changed every 2 to 3 days. hMSC were passaged at about 70% confluency when they were harvested using 0.25% Trypsin-EDTA (Gibco) for 5 mins at 37° C. Viability and cell count assays were performed with the automated NucleoCounter® NC-3000 (Chemometec). All cultures were maintained at 37° C. in a 5% CO2 humidified incubator (Thermo Scientific). See table below showing the well plate design.

| | | | | | | Chondrogenic medium | | | | | |
|---|---|---|---|---|---|---|---|---|---|---|---|
| | — | | +B2 | | +10% EBN | | +5% EBN | | +2.5% EBN | | +1.25% EBN |
| 1 | 2 | 3 | 4 | 5 | 6 | 7 | 8 | 9 | 10 | 11 | 12 |
| A | D 7 | D 21 | D 7 | D 21 | D 7 | D 21 | D 7 | D 21 | D 7 | D 21 | D 7 | D 21 |
| B | D 7 | D 21 | D 7 | D 21 | D 7 | D 21 | D 7 | D 21 | D 7 | D 21 | D 7 | D 21 |
| C | D 7 | D 21 | D 7 | D 21 | D 7 | D 21 | D 7 | D 21 | D 7 | D 21 | D 7 | D 21 |
| D | D 7 | D 21 | D 7 | D 21 | D 7 | D 21 | D 7 | D 21 | D 7 | D 21 | D 7 | D 21 |
| E | D 14 | D 28 | D 14 | D 28 | D 14 | D 28 | D 14 | D 28 | D 14 | D 28 | D 14 | D 28 |
| F | D 14 | D 28 | D 14 | D 28 | D 14 | D 28 | D 14 | D 28 | D 14 | D 28 | D 14 | D 28 |
| G | D 14 | D 28 | D 14 | D 28 | D 14 | D 28 | D 14 | D 28 | D 14 | D 28 | D 14 | D 28 |
| H | D 14 | D 28 | D 14 | D 28 | D 14 | D 28 | D 14 | D 28 | D 14 | D 28 | D 14 | D 28 |

Figure 10B:
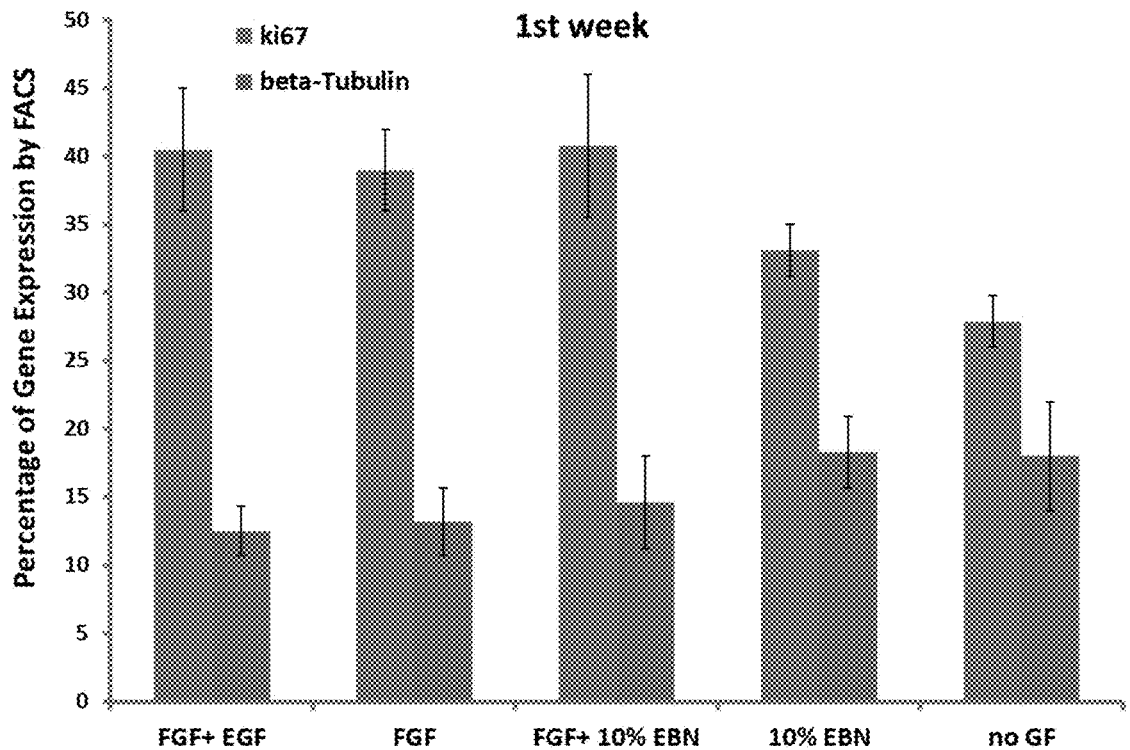

We carried out further analysis of the expanded hNPCs. As shown in FIG. 10B, the NPC culture with FGF-2 and EBN extract exhibited similar population of cells expressing the cellular proliferation marker, ki67 and neuronal differentiation marker, beta-Tubulin. EBN extract supplemented culture without FGF-2 exhibited lower ki67 and high beta-Tubulin cell population. The trend of ki67 was consisted to cell growth study where EBN extract could not support NPC growth without FGF-2. The low ki67 expression level is consistent to reported phenomena that the decreased cell proliferation occurred at the onset of neuronal differentiation.

Figure 11A:
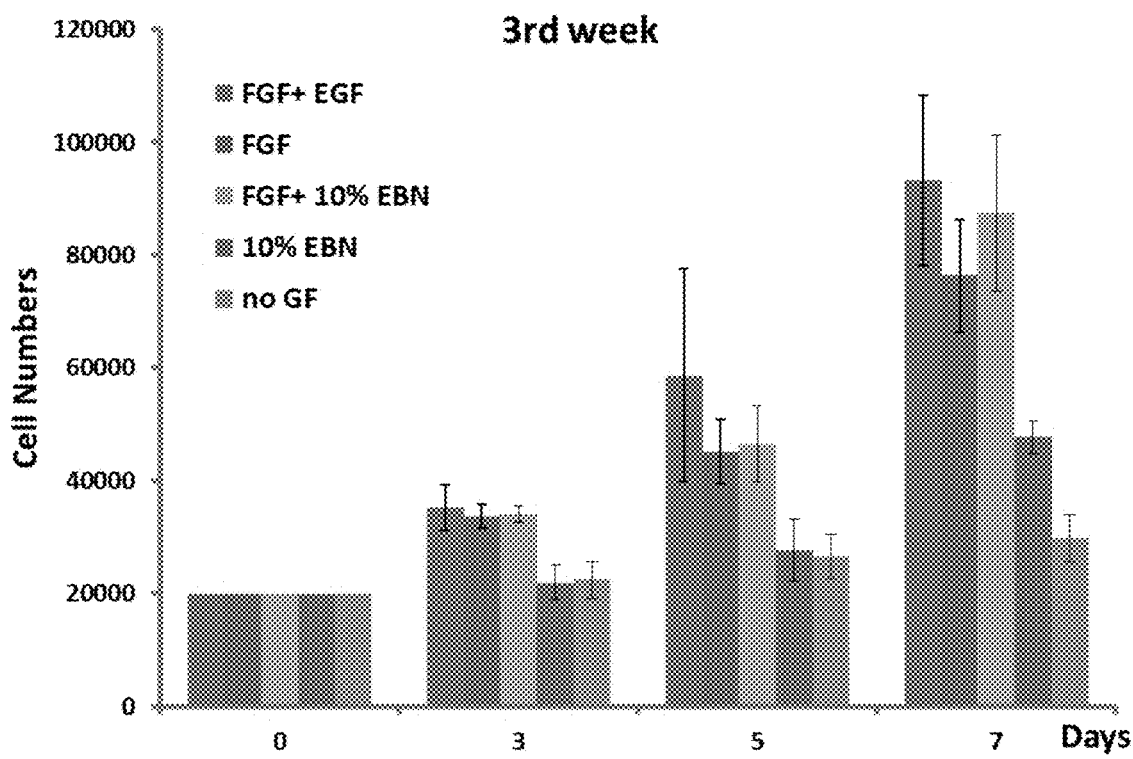
Figure 11B:
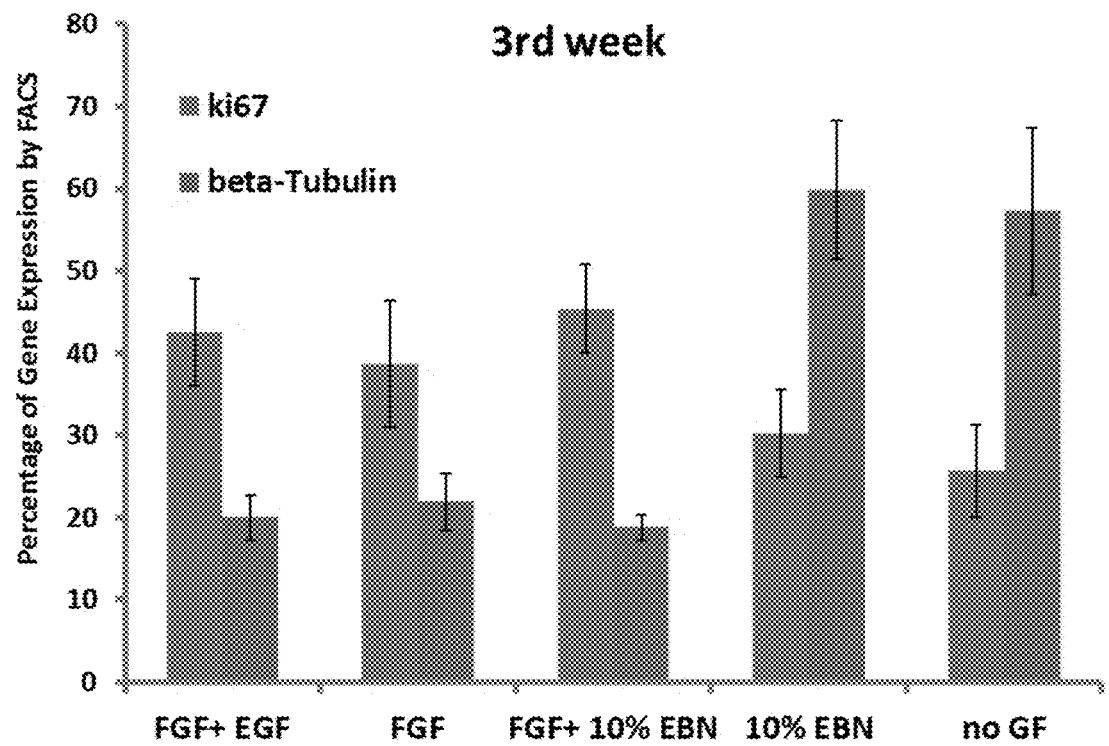
Figure 12:
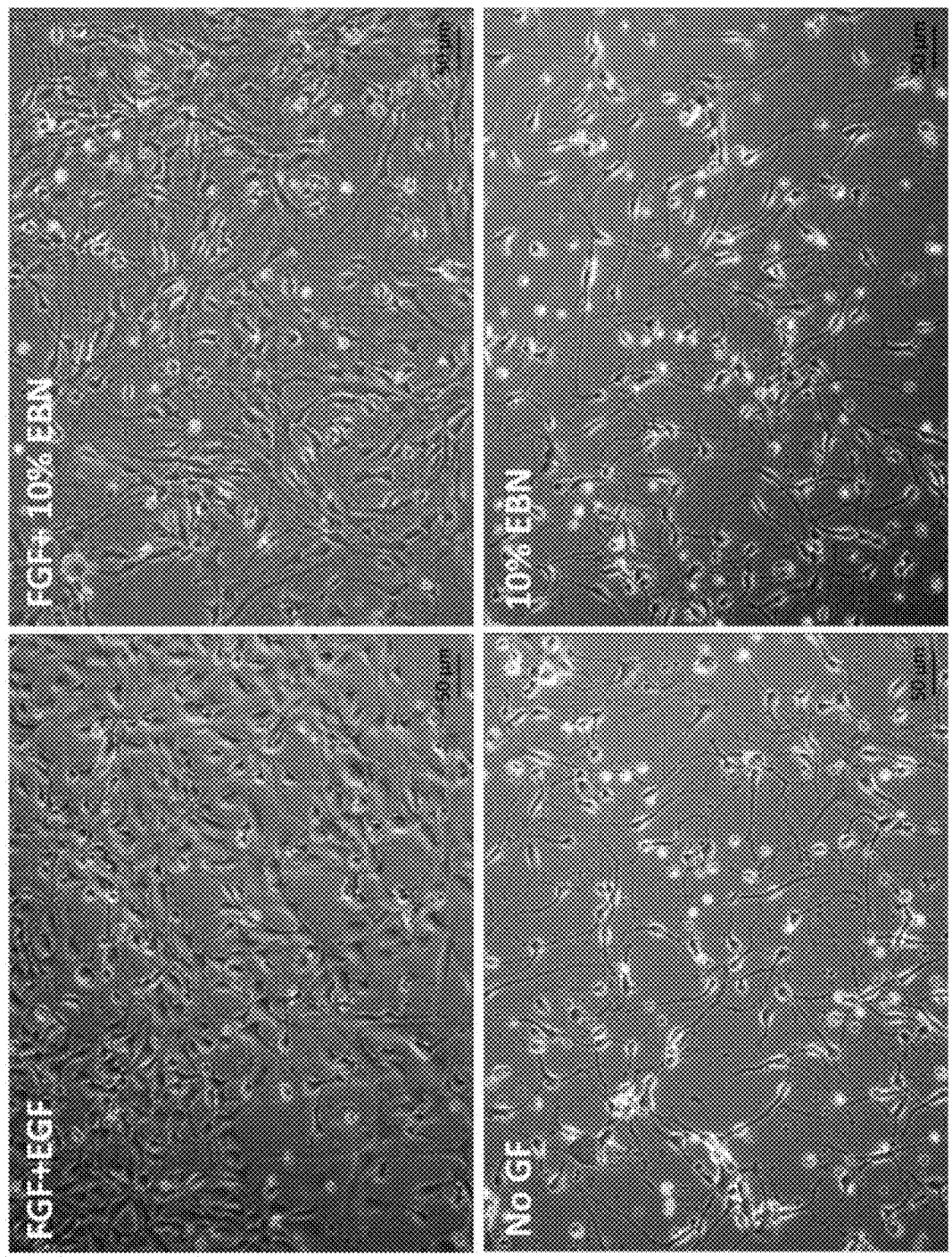
Figure 13:
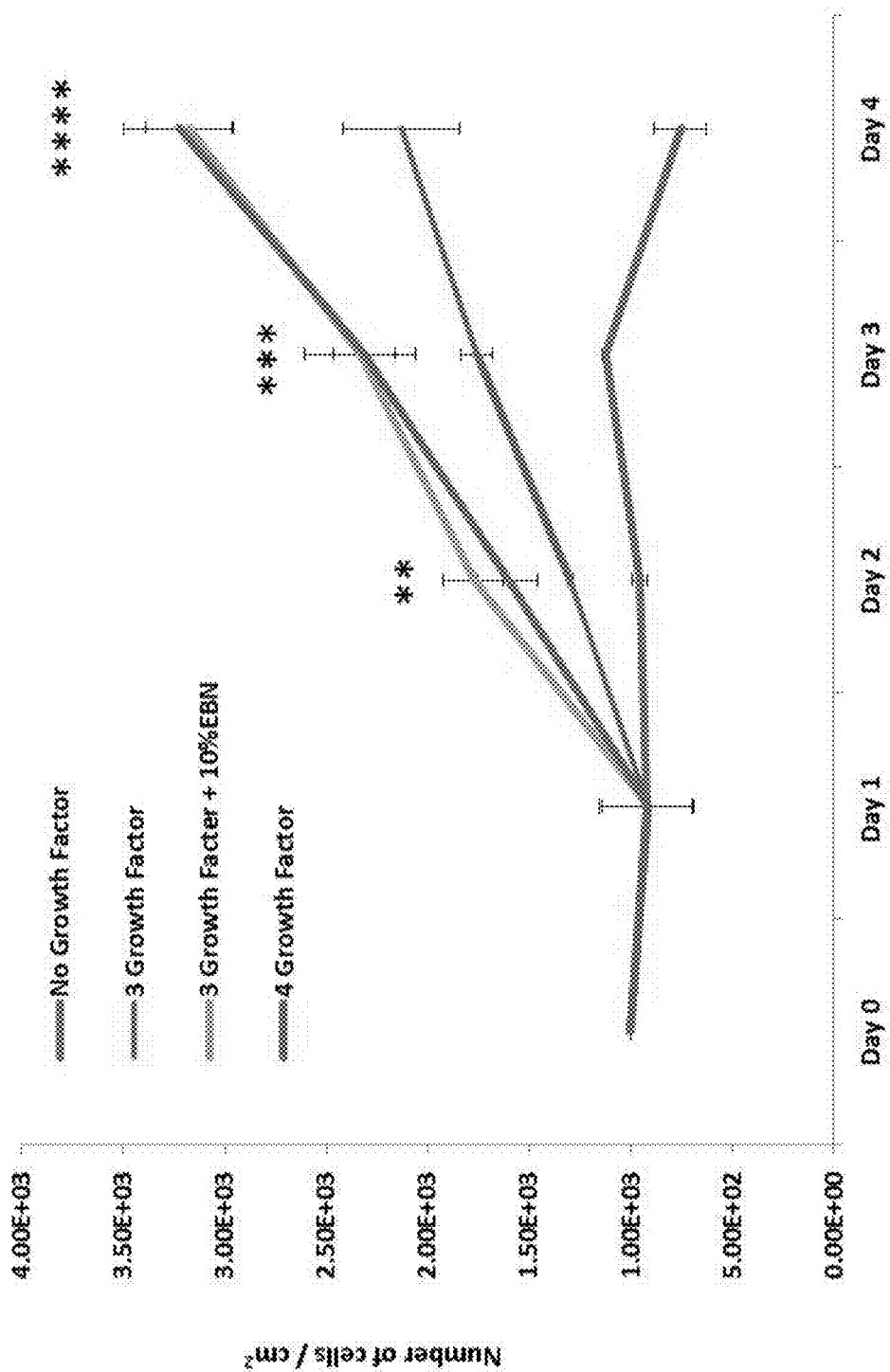
Figure 14:
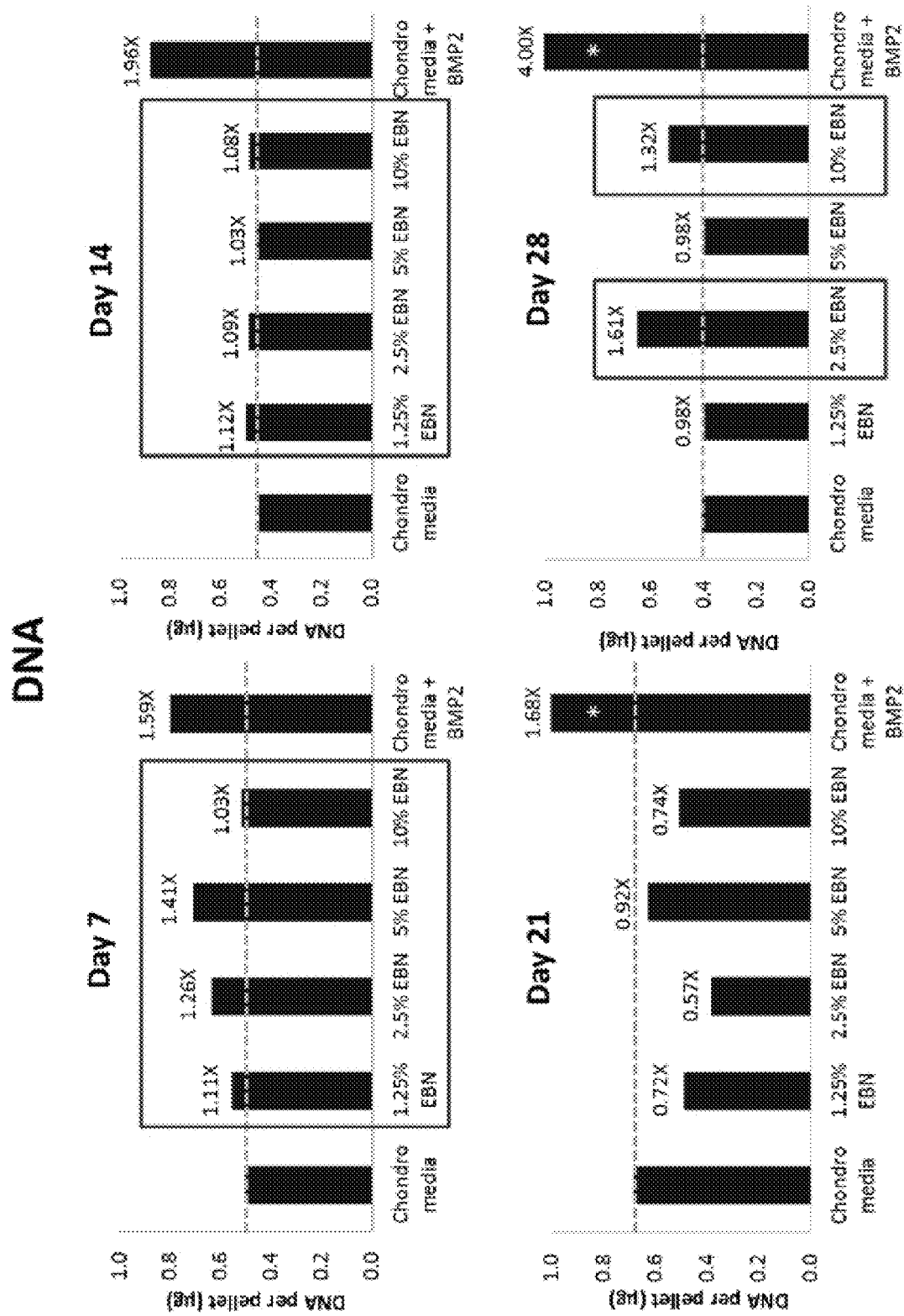
Figure 15:
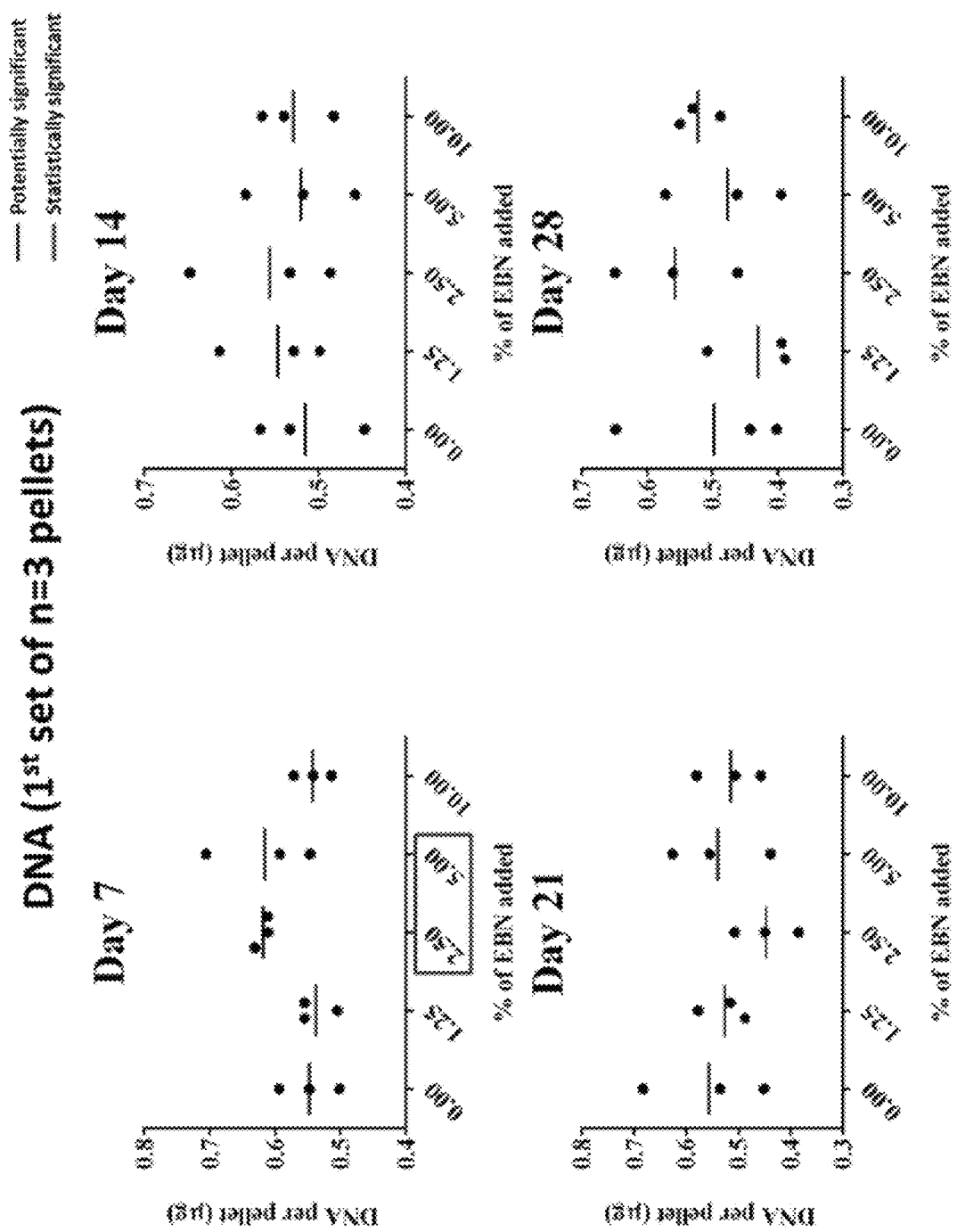
Figure 16:
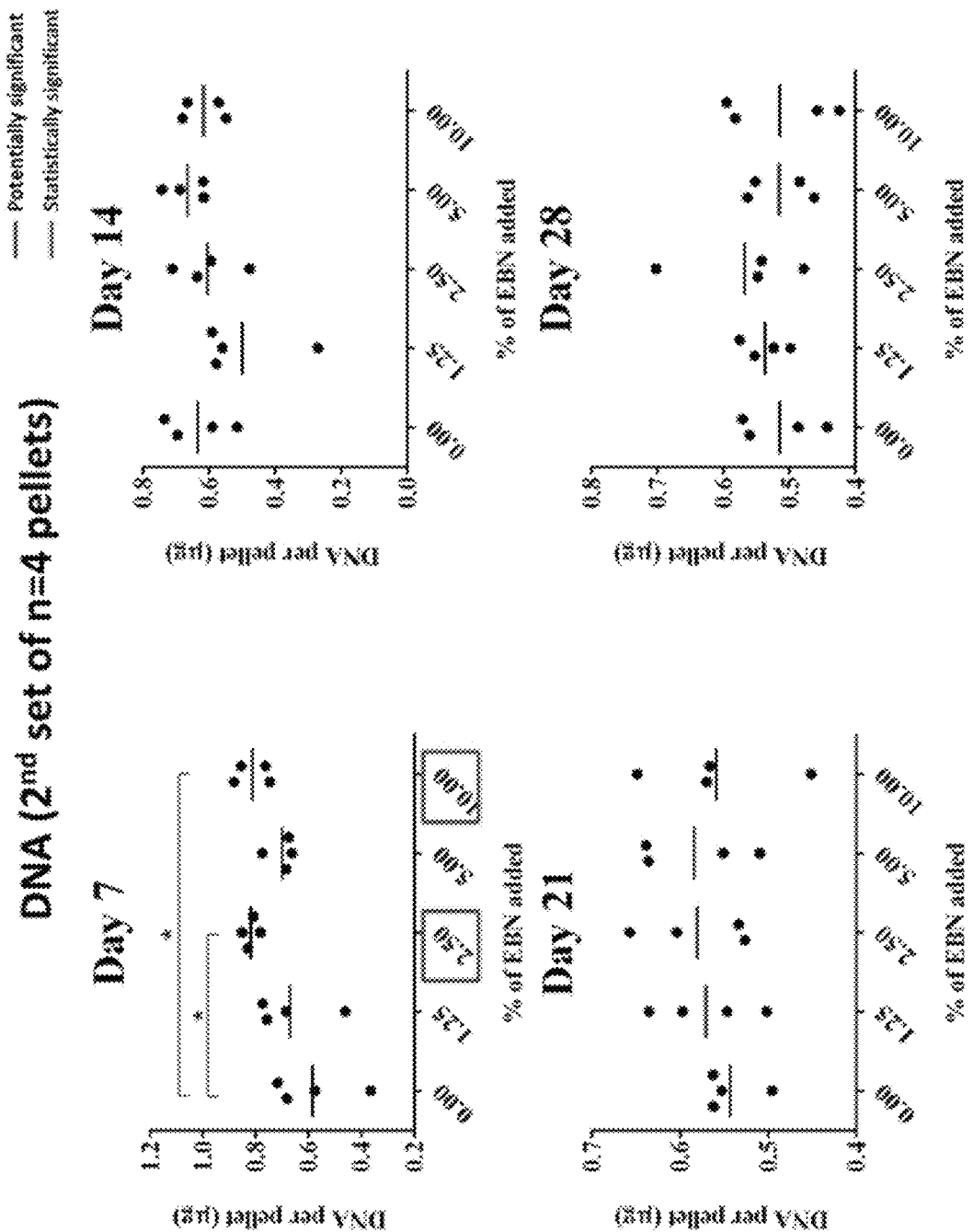
Figure 17:
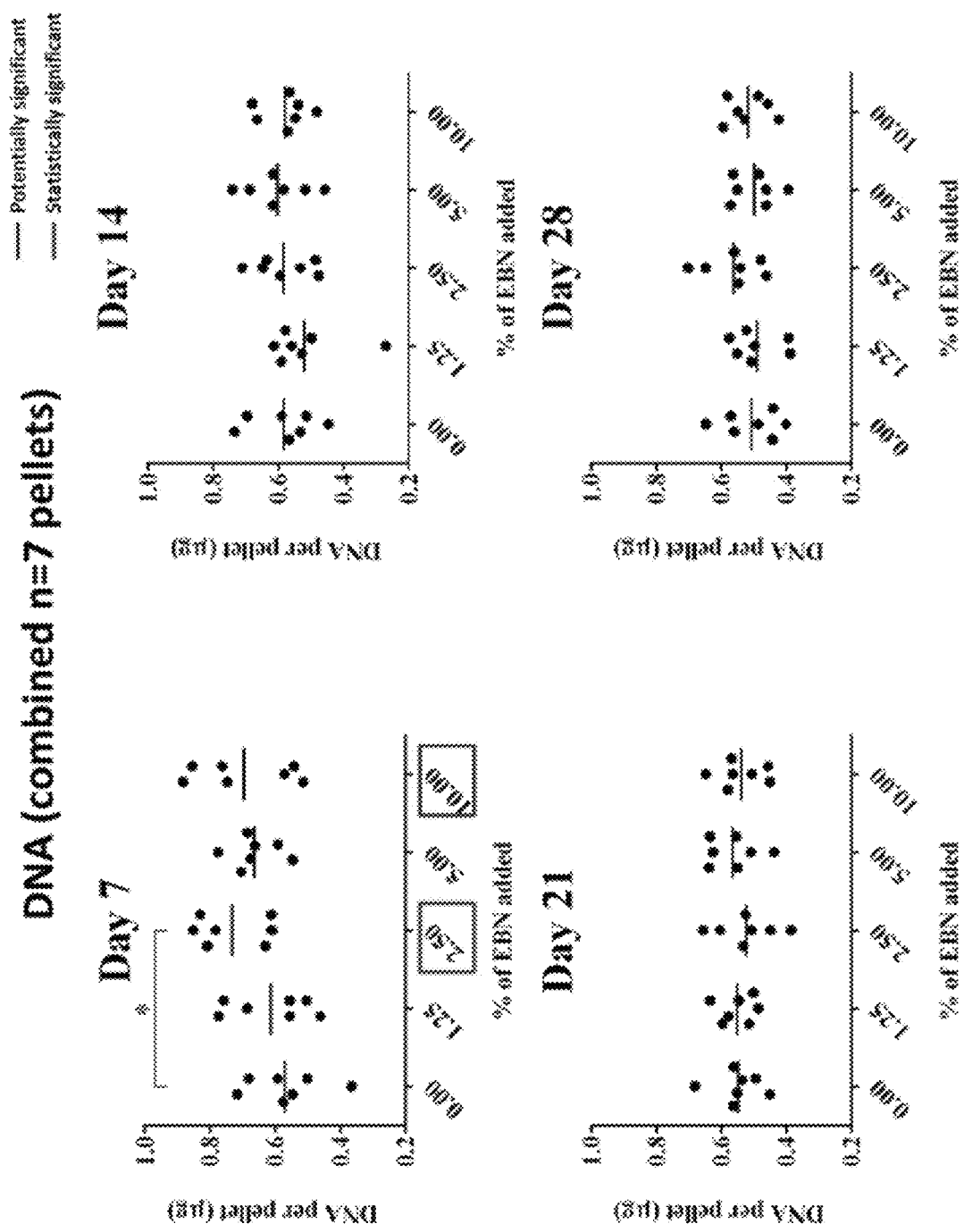
Figure 18:
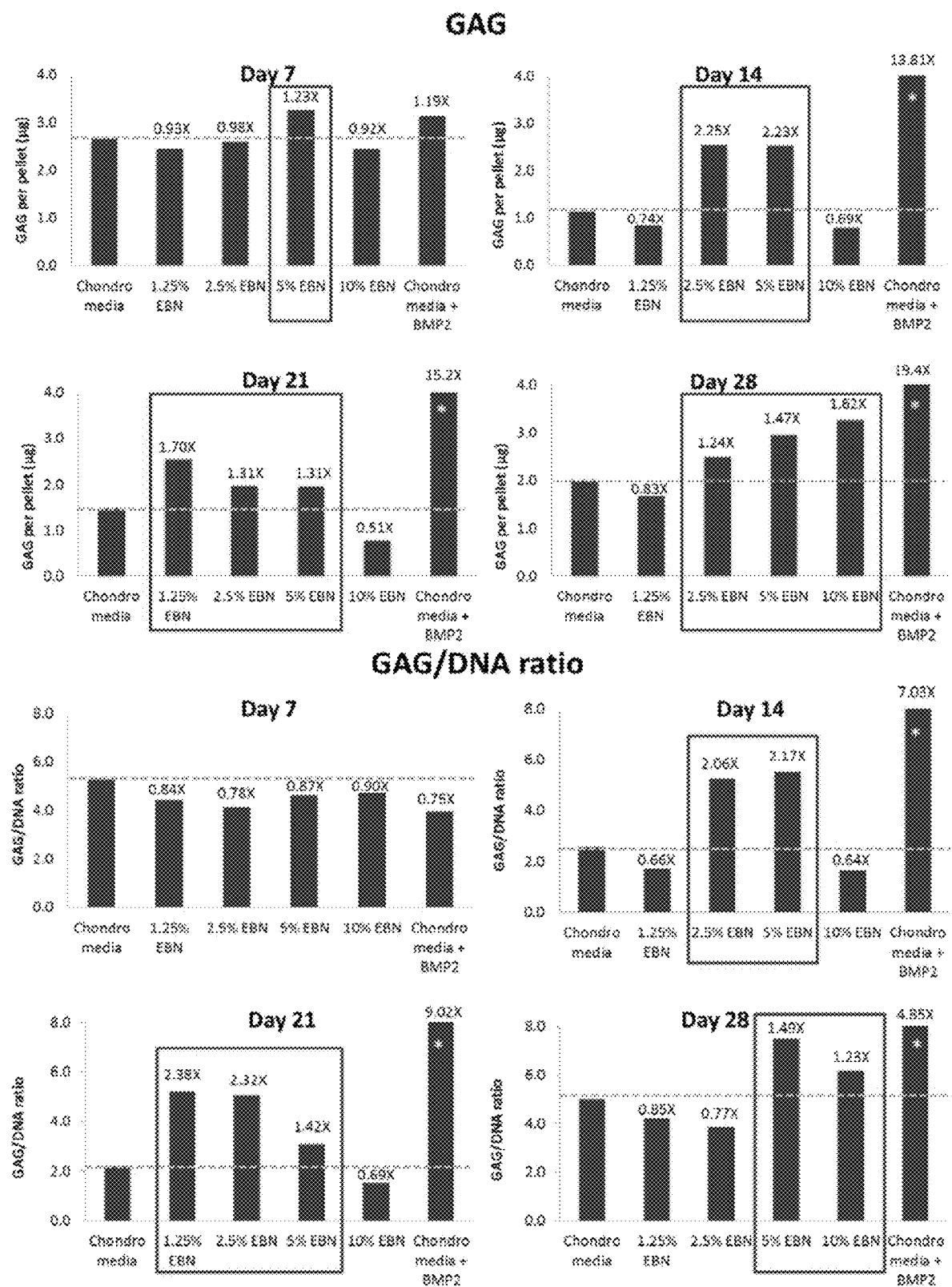
FIG. 18 Addition of the present EBN extracts lead to an increase in glycosaminoglycan (GAG) content per pellet and GAG/DNA ratio, mostly from day 14 to day 28 of differentiation. The increase in GAG content per pellet is most significant and most consistent from day 14 to day 28 of differentiation using 2.5% to 5%. The increase in GAG/DNA ratio is most significant and most consistent from day 14 to day 28 of differentiation using 5% of EBN. GAG is a major type of proteoglycan commonly found in cartilage tissue. GAG content per pellet is indicative of the total functional output of stem cell-derived chondrocyte-like cells in vitro. GAG/DNA ratios reflect GAG production per cell and are used as functional indicators of how well the stem cells are differentiating into chondrocyte-like cells. Dotted lines refer to GAG per pellet and GAG/DNA ratios when no EBN extracts were added. Numbers refer to the fold change induced over 0% of EBN. Boxes highlight those with fold increase more than 1.0.
Figure 19:
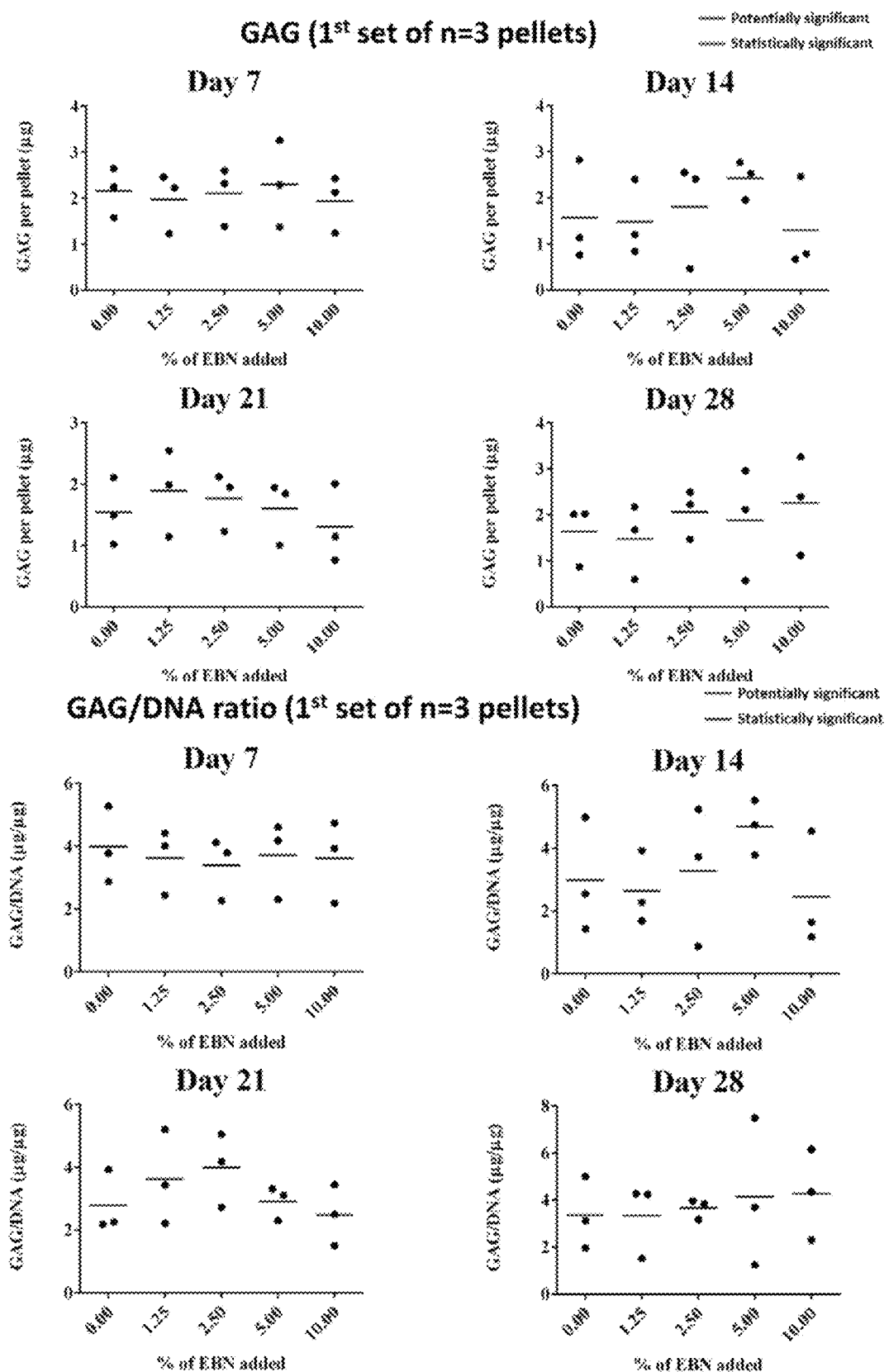
FIG. 19 For the first independent experiment of n=3 pellets in total, addition of the present EBN extracts did not lead to a statistically significant increase in GAG content per pellet and GAG/DNA ratio from day 7 to day 28 of differentiation. This is likely due to the variation in the GAG and DNA content (refer to FIG. 15) observed between pellets of the same condition at each indicated timepoint. GAG is a major type of proteoglycan commonly found in cartilage tissue. GAG content per pellet is indicative of the total functional output of stem cell-derived chondrocyte-like cells in vitro. GAG/DNA ratios reflect GAG production per cell and are used as functional indicators of how well the stem cells are differentiating into chondrocyte-like cells. Statistical analysis was performed with ordinary one-way ANOVA with Tukey's multiple comparisons test. Blue boxes highlight those that can be potentially significant if analysis can be done on more samples. Red boxes highlight those that are statistically significant.
Figure 20:
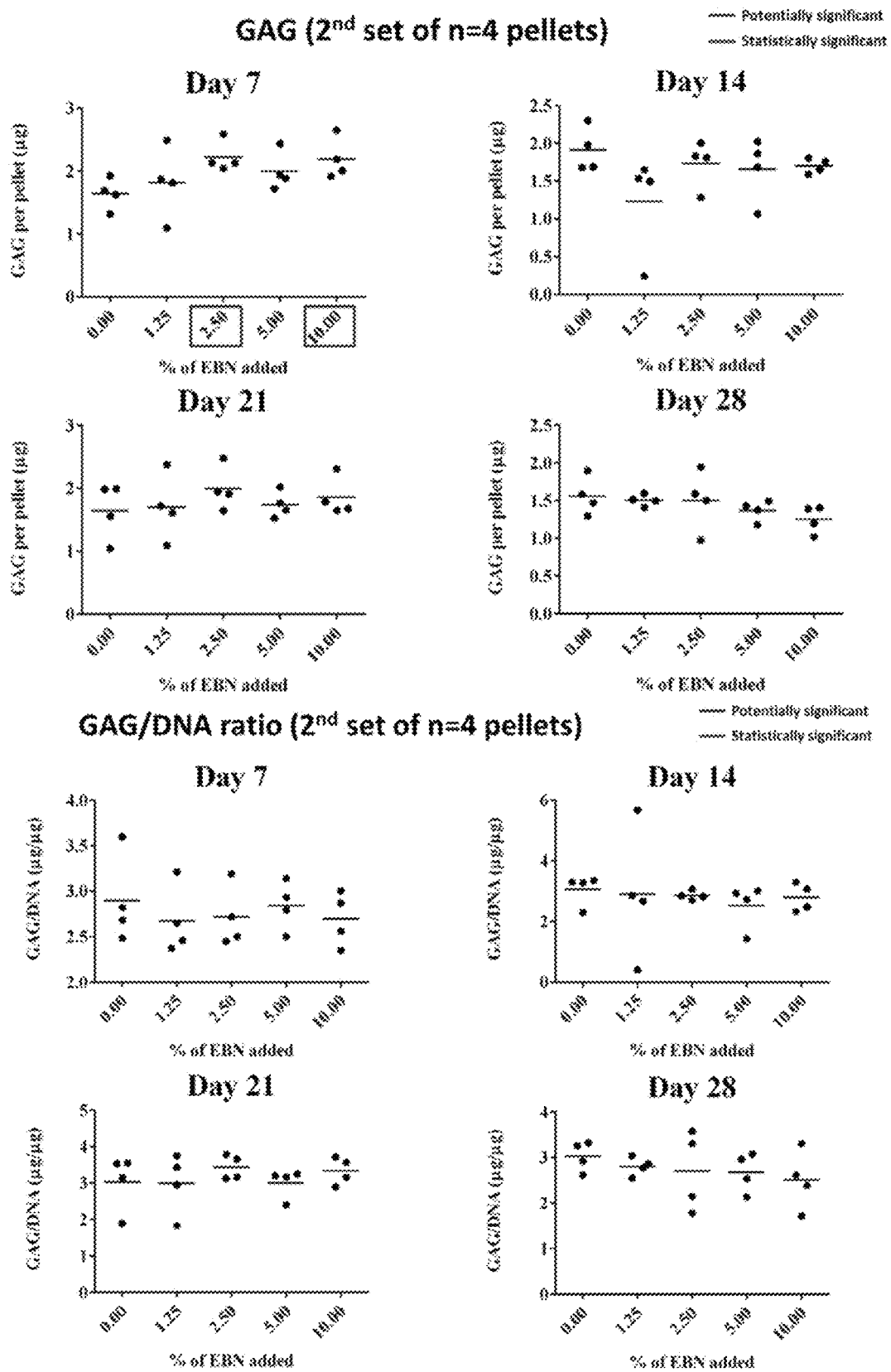
FIG. 20 For the second independent experiment of n=4 pellets in total, addition of the present EBN extracts did not lead to a statistically significant increase in GAG content per pellet and GAG/DNA ratio from day 7 to day 28 of differentiation. This is likely due to the variation in the GAG and DNA content (refer to FIG. 15) observed between pellets of the same condition at each indicated timepoint. However, 2.5% and 10% of the present EBN extracts could potentially lead to a statistically significant increase in GAG content per pellet at day 7 of differentiation, when compared to control conditions without any EBN extracts (0%). This could be due to the statistically significant increase in DNA content per pellet (refer to FIG. 16) as GAG/DNA content remains unchanged. GAG is a major type of proteoglycan commonly found in cartilage tissue. GAG content per pellet is indicative of the total functional output of stem cell-derived chondrocyte-like cells in vitro. GAG/DNA ratios reflect GAG production per cell and are used as functional indicators of how well the stem cells are differentiating into chondrocyte-like cells. Statistical analysis was performed with ordinary one-way ANOVA with Tukey's multiple comparisons test. Blue boxes highlight those that can be potentially significant if analysis can be done on more samples. Red boxes highlight those that are statistically significant.
Figure 21:
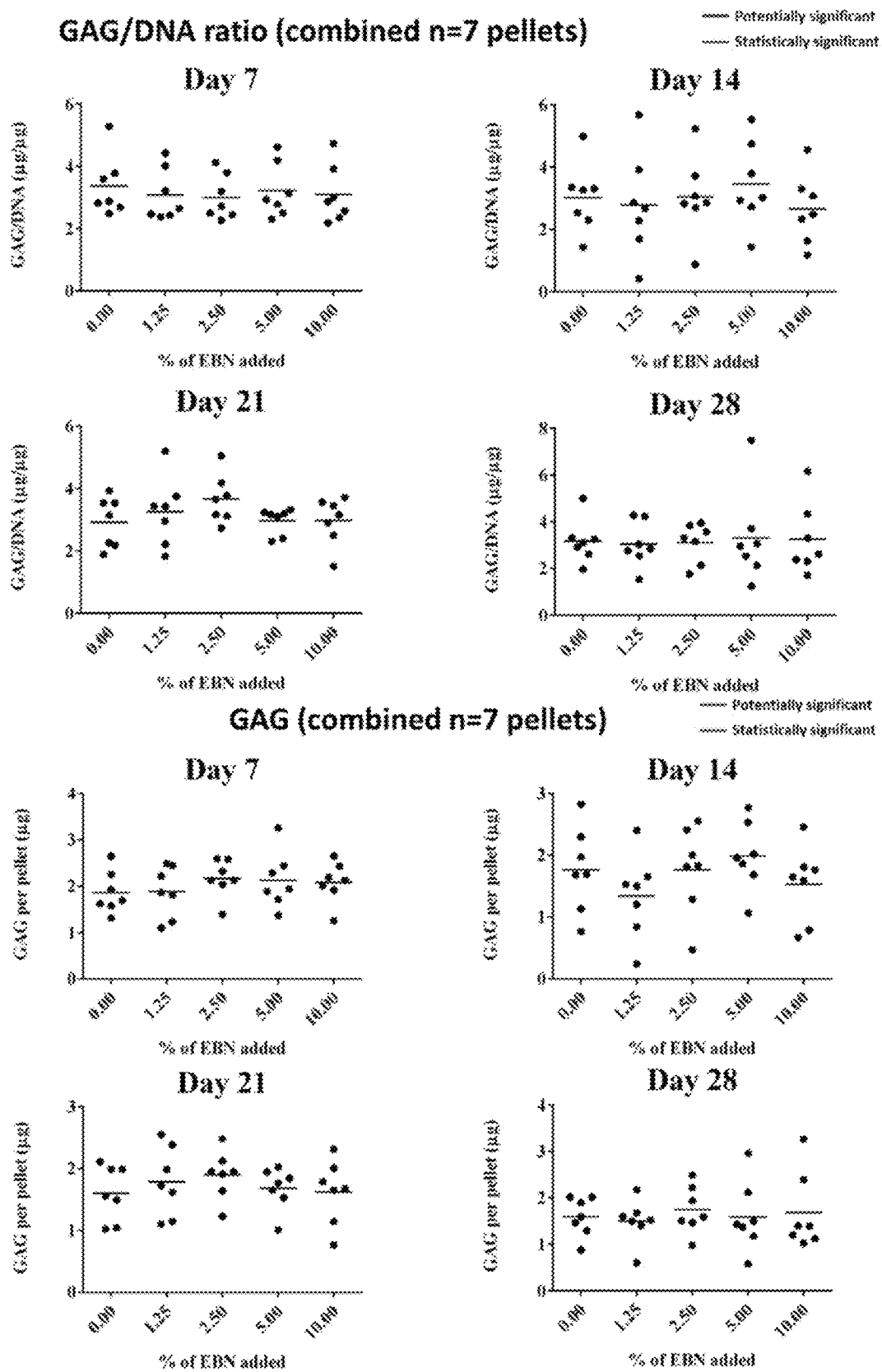
FIG. 21 For the combined results of n=7 pellets in total, addition of the present EBN extracts did not lead to a statistically significant increase in GAG content per pellet and GAG/DNA ratio from day 7 to day 28 of differentiation. This is likely due to the variation in the GAG and DNA content (refer to Figure. 2.2.2.) observed between pellets of the same condition at each indicated timepoint. GAG is a major type of proteoglycan commonly found in cartilage tissue. GAG content per pellet is indicative of the total functional output of stem cell-derived chondrocyte-like cells in vitro. GAG/DNA ratios reflect GAG production per cell and are used as functional indicators of how well the stem cells are differentiating into chondrocyte-like cells. Statistical analysis was performed with ordinary one-way ANOVA with Tukey's multiple comparisons test. Blue boxes highlight those that can be potentially significant if analysis can be done on more samples. Red boxes highlight those that are statistically significant.
Figure 22:
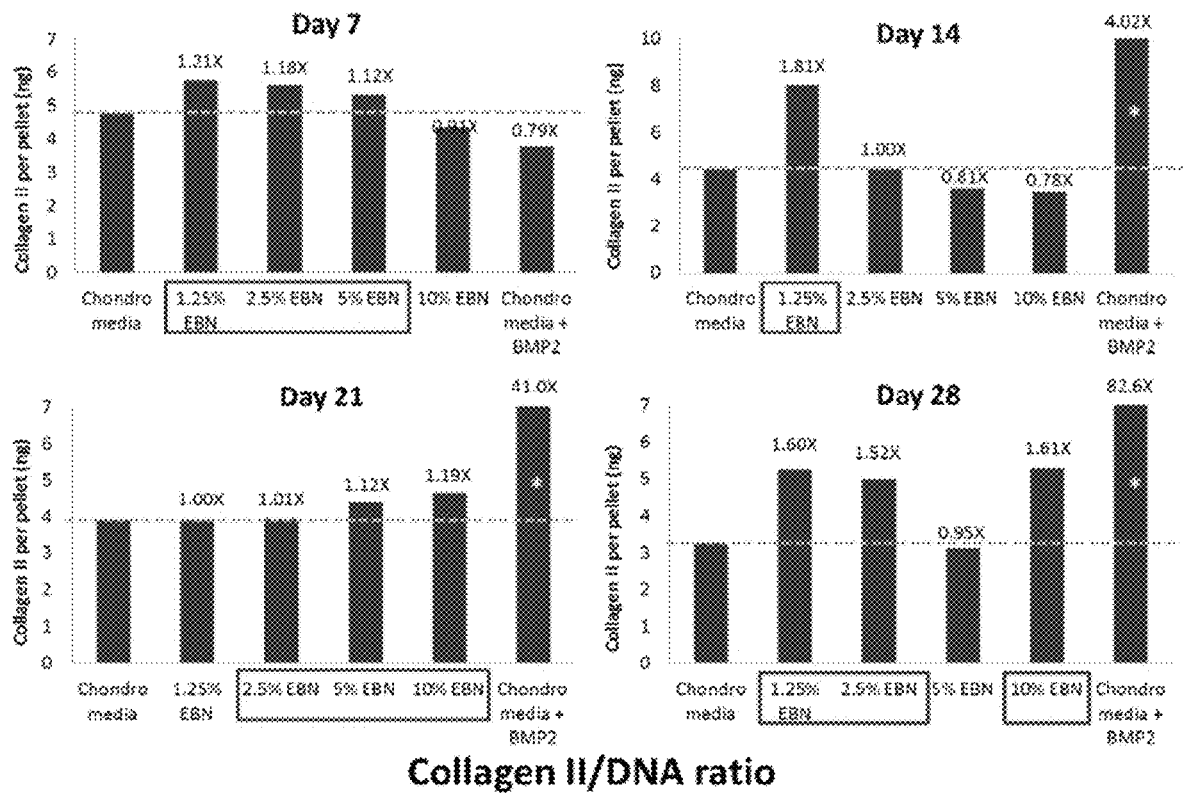
FIG. 22 Addition of the present EBN extracts lead to an increase in Collagen II content per pellet and Collagen II/DNA ratio, mostly from day 21 to day 28 of differentiation. The increase in Collagen II content per pellet is most significant and most consistent for 1.25% EBN from day 7 to day 14, as well as for 2.5% EBN from day 21 to day 28 of differentiation. The increase in Collagen II/DNA ratio is most significant and most consistent from day 7 to day 28 of differentiation using 1.25% EBN. Collagen II is a major type of collagen molecule or fibrils commonly found in articular cartilage tissue. Collagen II content per pellet is indicative of the total functional output of stem cell-derived chondrocyte like cells in vitro. Collagen II/DNA ratios reflect Collagen II production per cell and are used as functional indicators of how well the stem cells are differentiating into chondrocyte-like cells. Dotted lines refer to Collagen II per pellet and Collagen II/DNA ratios when no EBN extracts were added. Numbers refer to the fold change induced over 0% of EBN. Boxes highlight those with fold increase more than 1.0.
Figure 22:
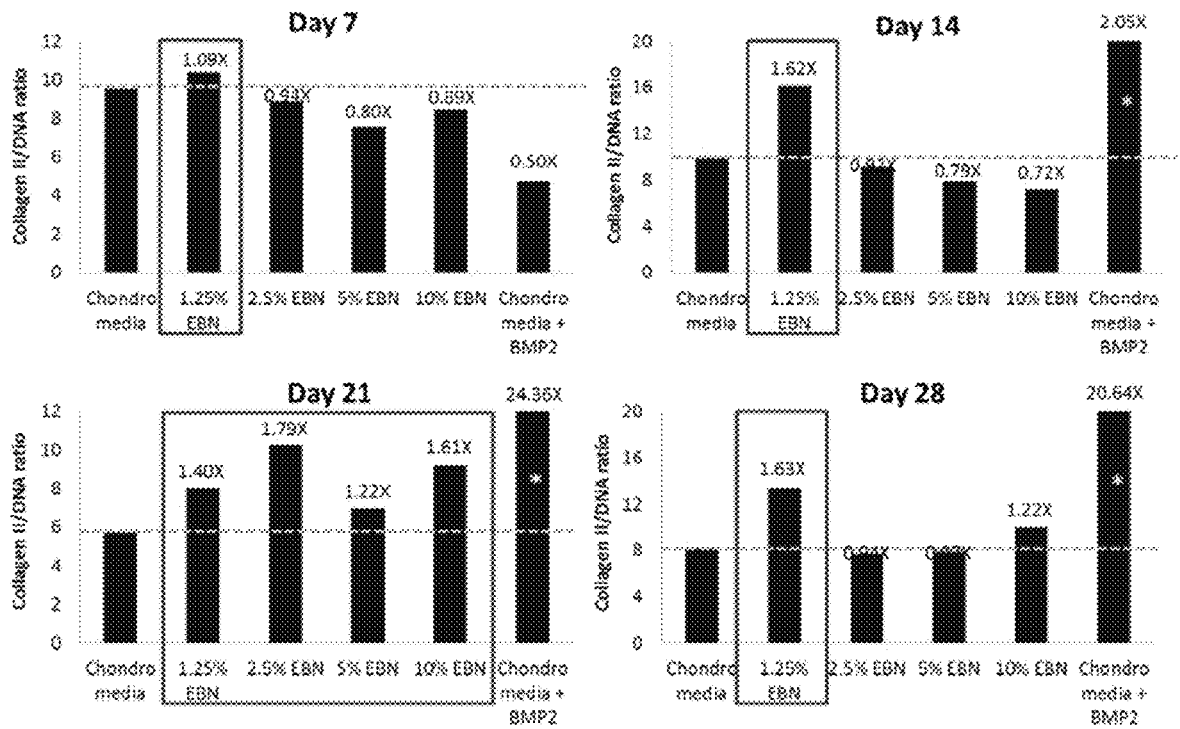
Figure 23:
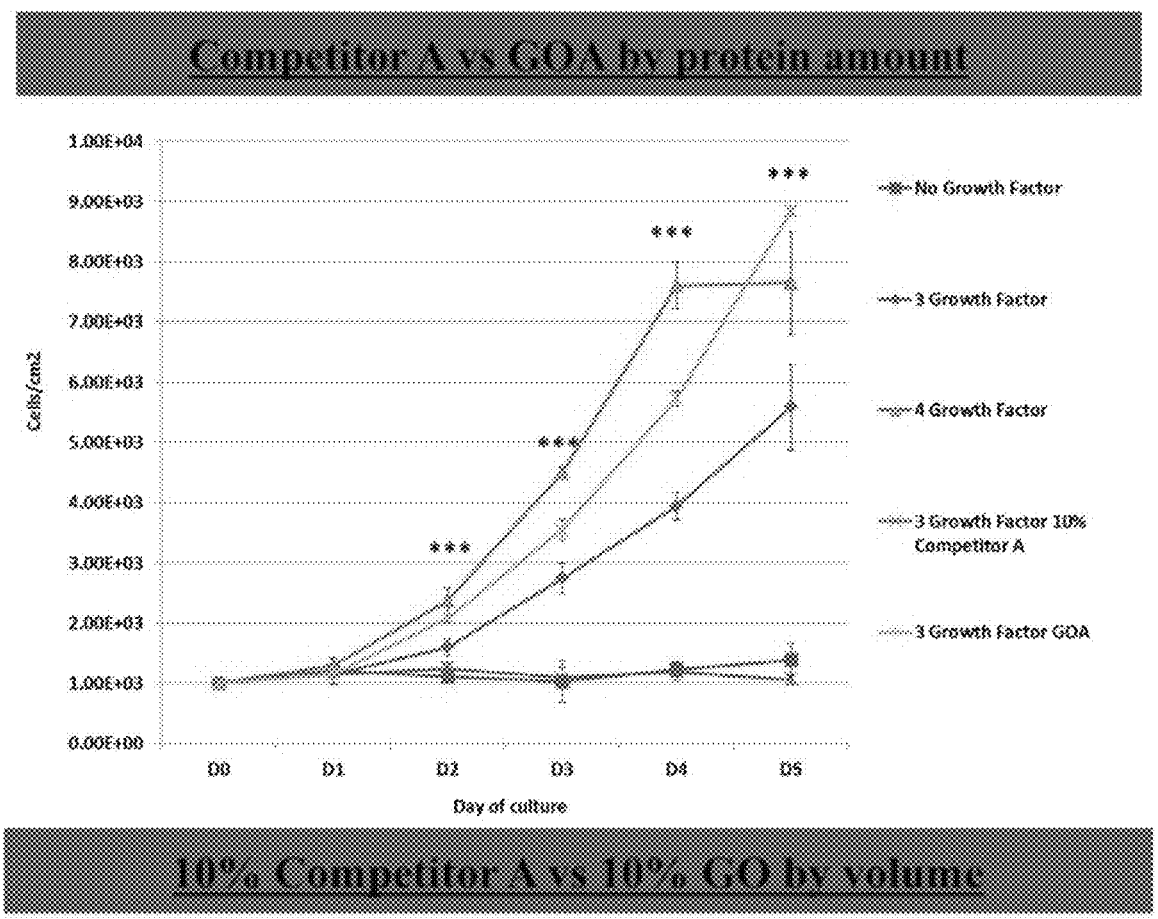
FIG. 23 Both 4.39% and 10% of the present EBN extracts are significantly better than 10% Competitor A EBN in inducing hMSC cell growth from day 2 through day 5 of culture. Surprisingly, 3 Growth Factor+10% Competitor A has a cell growth curve that (i) is significantly different from that of 3 Growth Factor only ($p<0.05$ for day 2, $p<0.001$ for all other days), (ii) is significantly different from that of 4 Growth Factor ($p<0.001$ for all days), and (iii) is not significantly different from that without growth factors ($p>0.05$ for all days). This shows that Competitor A EBN (i) has an inhibitory effect that negates the effect of the other 3 growth factors, (ii) cannot replace EGF to achieve a growth curve similar to 4 growth factors, and (iii) is not inducing cell growth which also implies that Competitor A EBN may be causing cell death instead. The statistical analysis for this set of results is not shown on the graph and is accomplished separately. Most importantly, comparing the present EBN extracts (GOA) to Competitor A EBN by protein amount revealed that 4.39% of the present EBN extracts can induce a cell growth curve that is statistically significantly different from 10% Competitor A EBN, starting from day 2 through day 5 of culture (*** $p<0.001$ for all days; p values are shown on the graph). Similarly, comparing the present EBN extracts (GOA) to Competitor A EBN by volume revealed that 10% the present EBN extracts can induce a cell growth curve that is statistically significantly different from 10% Competitor A EBN, starting from day 2 through day 5 of culture (p values are shown on the graph). This is significant and novel as it shows that the present EBN extracts are more potent than Competitor A EBN in (i) promoting cell growth and not causing cell death like that of Competitor A, and (ii) its ability to replace EGF.
Figure 23:
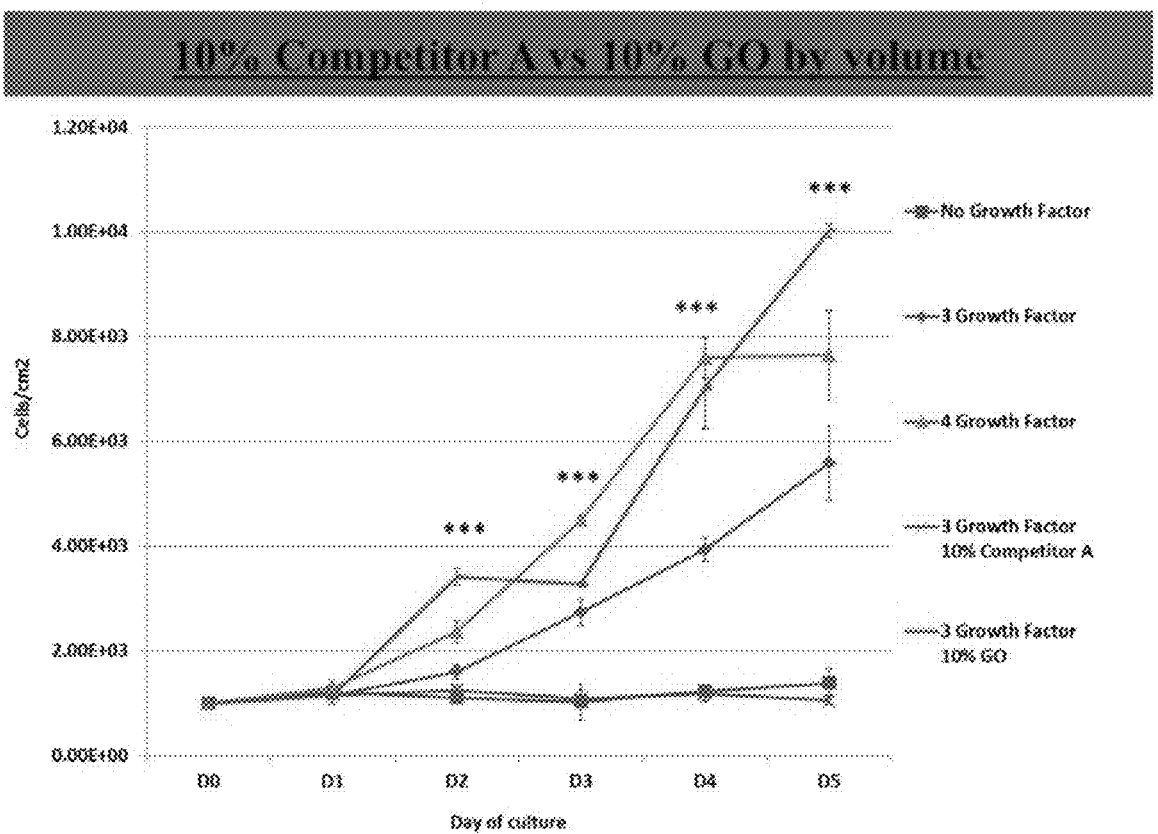
Figure 24:
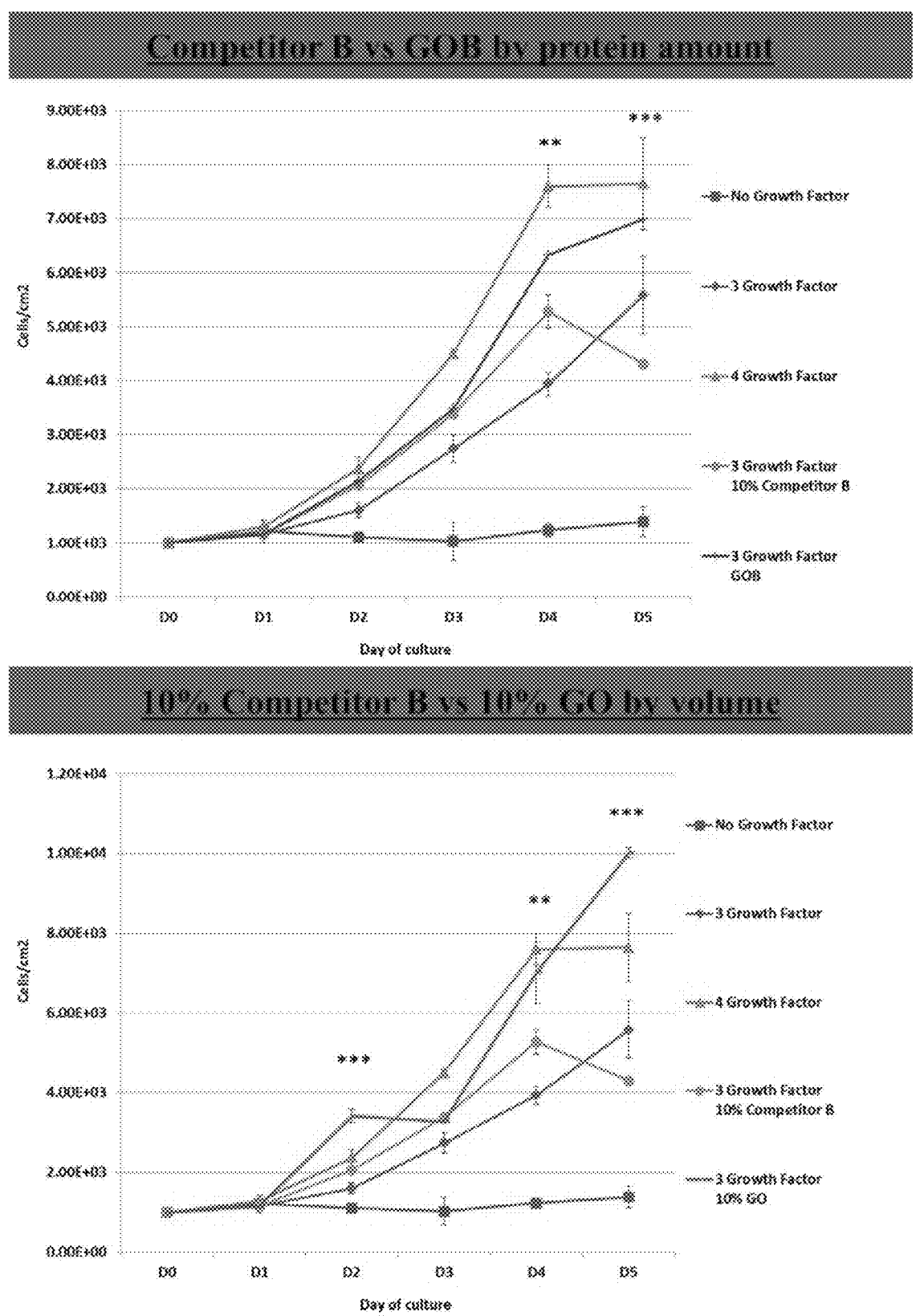
FIG. 24 Both 3.35% and 10% of the present EBN extracts are significantly better than 10% Competitor B EBN in inducing hMSC cell growth, from day 4 to day 5 and from day 2 through day 5 of culture respectively. Surprisingly, 3 Growth Factor+10% Competitor B has a cell growth curve that (i) is significantly different from that of 3 Growth Factor only from day 2 through day 4 ($p<0.01$ for day 2, $p<0.05$ for day 3, $p<0.001$ for day 4), (ii) is significantly different from that of 4 Growth Factor ($p<0.01$ for day 3, $p<0.001$ for day 4 and 5), and (iii) is significantly different from that without growth factors ($p<0.001$ for all days). This shows that Competitor B EBN (i) has a significant positive effect on cell growth only from day 2 to day 4 when compared to that of 3 growth factors only, (ii) cannot replace EGF to achieve a growth curve similar to 4 growth factors from day 3 through day 5 of culture, and (iii) is not inducing cell death as compared to that of no growth factors. The statistical analysis for this set of results is not shown on the graph and is accomplished separately. Most importantly, comparing the present EBN extracts (GOB) to Competitor B EBN by protein amount revealed that 3.35% GeneOasis EBN can induce a cell growth curve that is statistically significantly different from 10% Competitor B EBN, starting from day 4 through day 5 of culture ( $p<0.01$ for day 4 and * $p<0.001$ for day 5; p values are shown on the graph). Similarly, comparing the present EBN extracts (GOB) to Competitor B EBN by volume revealed that 10% of the present EBN extracts can induce a cell growth curve that is statistically significantly different from 10% Competitor A EBN, starting from day 2 through day 5 of culture ( $p<0.01$ for day 4 and * $p<0.001$ for day 2 and day 5; p values are shown on the graph). This is significant and novel as it shows that the present EBN extracts are more potent than Competitor B EBN in (i) promoting cell growth, and (ii) its ability to replace EGF, particularly at later stages of cell growth (day 4 and day 5 of culture).
Figure 25:
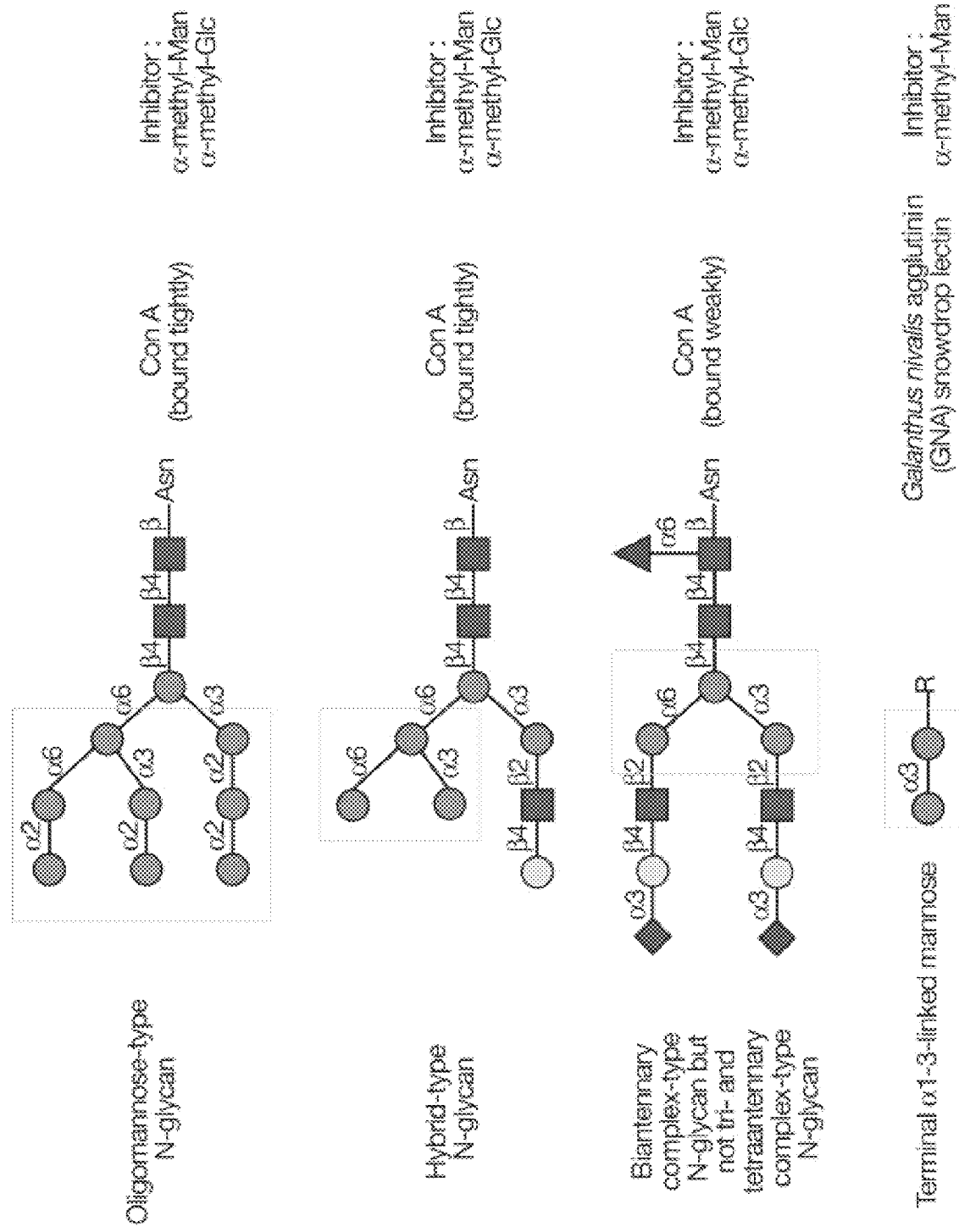
FIG. 25 depicts Oligomannose-type N-glycan, Hybrid-type N glycan, Biantennary complex-type N-glycan but not tri- and tetraantennary complex-type N-glycan, and Terminal α1-3-linked mannose.
Figure 26:
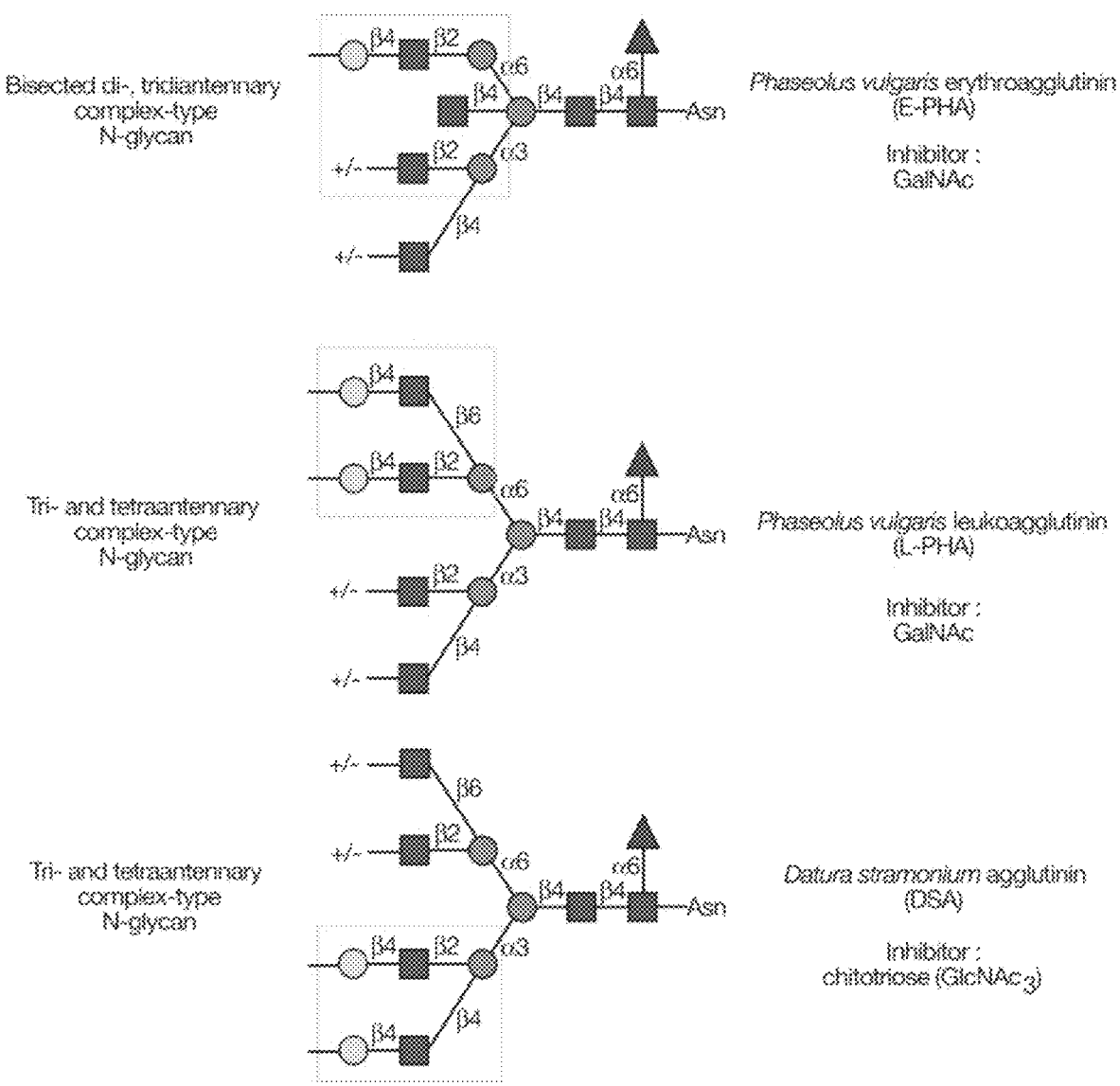
FIG. 26 depicts Bisected di-, tridiantennary complex-type N-glycan, Tri- and tetraantennary complex-type N-glycan, and Tr- and tetraantennary complex-type N-glycan.

We have extended the study to three weeks. As shown in FIG. 11, EBN extracts combined with FGF-2 seemed to exhibit higher cell yield than the cultures with FGF-2 only. The expressions of cell proliferation marker ki67 were similar to the earlier culture in all conditions. However, we found that neuronal differentiation marker (beta-Tubulin) was significantly increased in hNPC culture supplemented with EBN extracts without FGF-2 and reached a similar level to the culture without both EGF and FGF-2. The increased Betatubulin positive cell population indicated the development of neuronal cells. This was consistent with the cell morphology images shown in FIG. 12, where neuronal cell morphology (neurite extensions) became significant in cultures with high beta-Tubulin expression. hNPC maintained their typical morphology when grown on the condition of 10% EBN extracts+ FGF.

In conclusion, our study indicates the present EBN extracts contain EGF-like component, which can be beneficial to long term culturing of hNPC. One of the future studies may be considered is the fractionation of the EBN extract to isolate the EGFlike component for further characterization.

Effect of EBN's Extract on Cell Culture, Cell Growth and Chondrogenic Assays 1.2.1. hMSC Cell Culture hMSC (passage 8 to 9) were plated at a density of 2400 to 2800 cells/cm$^2$ in either T175 cm$^2$ cell culture flasks or Nunc™ EasyFill™ Cell Factory™ Systems in MSC growth medium consisting of Minimum Essential Medium a, 10%

1.2.2. hMSC Cell Expansion for Cell Growth Curve hMSC were plated at a density of 1000 cells/cm$^2$ in Nunclon™ Delta Surface 24-well plates. hMSC was seeded at day 0 and cultured for 4 days. hMSC grown only in BTI's proprietary serum-free MSC growth medium without any growth factors and GeneOasis Pte Ltd's EBN extracts were used as negative controls, and were known as "No Growth Factors". hMSC grown in BTI's proprietary serum-free MSC growth medium supplemented with 10 ng/ml of PDGF (Peprotech), 5 ng/ml of TGFß-1 (Peprotech), and 10 ng/ml of FGFß (Gibco) were also used as negative control, also referred to as "3 Growth Factors". hMSC grown in BTI's proprietary serum-free MSC growth medium supplemented with 10 ng/ml of PDGF (Peprotech), 5 ng/ml of TGFR-1 (Peprotech), 1 ng/ml of EGF (Peprotech) and 10 ng/ml of FGFß (Gibco) were used as positive control, also referred to as "4 Growth Factors". hMSC grown in serum-free MSC growth medium supplemented with 3 growth factors (excluding EGF) with 10% EBN (vol/vol) were tested and was referred to as "3 Growth Factors+10% EBN". 10% (vol/vol) EBN was added on day 1. Cell count assays were performed daily with triplicates for each condition with the automated NucleoCounter® NC-3000 (Chemometec). All cultures were maintained at 37° C. in a 5% CO2 humidified incubator (Thermo Scientific).

1.2.3. Chondrogenic Differentiation hMSC were grown as micromass pellets in clear round bottom ultra-low attachment 96 well plates (Corning) for chondrogenic differentiation. Pellets were formed by centrifugation at 1000 rpm for 5 mins at room temperature (rtm) using 2×105 hMSC per pellet per well. They were cultured in chondrogenic differentiation medium containing DMEM-high glucose (Gibco), 1 mM sodium pyruvate (Gibco), 100 nM dexamethasone (Sigma), 0.1 mM L-ascorbic acid-2-phosphate (Sigma), 1% ITS+1 (Sigma), L-proline (Sigma) and 1% Penicillin/Streptomycin (Gibco). Pellets grown only in chondrogenic differentiation medium without the present invention's extracts were used as negative controls. Pellets grown in chondrogenic differentiation medium with different concentrations of EBN (1.25%, 2.5%, 5% and 10% vol/vol) were tested. Pellets grown in chondrogenic differentiation medium supplemented with 100 ng/ml of BMP2 were used as positive controls. Chondrogenic medium with or without supplementation was changed every 2 to 3 days.

1.2.4. DNA, GAG and Collagen II Content Evaluation

Pellets (at least 3 per condition per timepoint) were rinsed once with Phosphate Buffer Saline (PBS) before immediate storage at −80° C. After thawing, the pellets were either digested with 0.125 mg/ml papain at 65° C. overnight for DNA and GAG quantification, or with 0.1 mg/ml pepsin at 4° C. over 2 nights followed by 0.1 mg/ml elastase digestion at 4° C. overnight for Collagen II evaluation. DNA quantification was done using Quant-iT Picogreen dsDNA Assay, GAG measurement was done using Blyscan Sulfated Glycosaminoglycan Assay (Biocolor), and Collagen II quantification was done by ELISA against Type II Collagen (Chondrex), all in accordance with manufacturer's instructions. All fluorometric and optical readings were taken at with Tecan Infinite M200.

1.2.5. Statistical Analyses

Data were analyzed with statistical software Prism 6 (GraphPad). Multiple comparisons among different conditions were compared statistically using ordinary one-way analysis of variance (ANOVA) with Tukey's multiple comparisons test. For all statistical tests, p values less than 0.05 were considered significant.

1.2.6. Comparison of the Present EBN Extract with Competitor A EBN and Competitor B EBN hMSC were grown in a similar fashion as detailed in 1.2.2. hMSC was seeded at day 0 and cultured for 5 days. 2 types of comparison of the present EBN extract to either Competitor A EBN or Competitor B EBN were performed. One type of comparison was to compare 10% of competitor EBN to the present EBN extract by normalizing or controlling for protein content (i.e. the present EBN extract control would have same amount of protein as that of the respective competitor). As measured, 10% of Competitor A EBN is equivalent to 4.39% of the present EBN extract. Thus, MSC growth medium supplemented with 3 growth factors (excluding EGF) with 4.39% GeneOasis EBN (vol/vol) were tested and was referred to as "GOA". MSC growth medium supplemented with 3 growth factors (excluding EGF) with 10% EBN of Competitor A (vol/vol) were tested and was referred to as "3 Growth Factors+10% Competitor A".

Likewise for Competitor B, 10% of Competitor B EBN is equivalent to 3.35% of the present EBN extract. Thus, MSC growth medium supplemented with 3 growth factors (excluding EGF) with 3.35% of the present EBN extract (vol/vol) were tested and was referred to as "GOB". MSC growth medium supplemented with 3 growth factors (excluding EGF) with 10% EBN of Competitor B (vol/vol) were tested and was referred to as "3 Growth Factors+10% Competitor B". The second type of comparison was to compare 10% of competitor EBN to the present EBN extract by normalizing or controlling for volume (i.e. 10% of the present EBN extract would be compared to 10% of Competitor EBN by volume). The investigators are blinded to the identity of Competitor A and B throughout the execution and data analysis of the related experiments.

The table below is a summary of methods of comparison of the present EBN extract to either Competitor A EBN or Competitor B.

| GeneOasis vs Competitors A&B |
|---|
| Aim-To investigate if 10% of competitor A and B have the same effect of Gene Oasis EBN on cell growth in Serum free conditions (Normalized to total protein in media (ug/ml) or volume ratio of EBN in media) |
| Conditions |
| Cell line: hMSC<br>Media: In-house serum free media<br>Controls |
| 1) 4 growth factors (Positive control)<br>2) No growth factor (Negative control)<br>3) 3 growth factor only-No EGF (Baseline control)<br>3) Gene oasis control for compethor A (GOA)-Same amount of protein as Competitor A<br>4) Gene oasis control for competitor B (GOB)-Same amount of protein as Competitor B<br>According to Protein Concentrations from Gerine |
| 10% Competitor A EBN equivalent to 4.39% Gene Oasis EBN (GOA)<br>10% Competitor B EBN equivalent to 3.35% Gene Oasis EBN (GOB) |

2. Results

The present EBN extract can elicit an increase in human stem cell proliferation during cell expansion in vitro, as shown in the FIGS. 13 to 24.

Whilst there has been described in the foregoing description preferred embodiments of the present invention, it will be understood by those skilled in the technology concerned that many variations or modifications in details of design or construction may be made without departing from the present invention.

The invention claimed is:

1. A bird's nest extract comprising at least one molecule obtained from edible bird's nest (EBN) obtained from a method comprising the steps of:

(a) washing raw EBN;

(b) filtering the washed EBN;

(c) extracting the molecule from the EBN, wherein extracting the molecule is carried by exposing the washed EBN to any one of an extraction solution selected from the group consisting of:

(i) a solution comprising an anti-N glycan and an anti-O glycan;

(ii) a solution comprising an anti-heparan sulphate, an anti-chondroitin, an anti-keratan, and an anti-dermatan; and (iii) a solution comprising an anti-leucine zipper, an anti-helix-turn-helix, and an anti-zinc finger.

2. A composition comprising an extract according to claim 1.

3. The composition according to claim 2 further comprising a maltodextrin.

4. The composition according to claim 3, wherein the amount of maltodextrin present in the composition is between 30 wt % to 75 wt %.

5. The composition according to claim 1 for use in medicine.

6. A pharmaceutical composition comprising an extract according to claim 1 and a pharmaceutically-acceptable carrier, excipient or diluent.

* * * * *